US011932720B1

(12) United States Patent
Kriesel et al.

(10) Patent No.: US 11,932,720 B1
(45) Date of Patent: *Mar. 19, 2024

(54) FLEXIBLE MEDICAL ITEM CONTAINER

(71) Applicant: Universal Tech Corporation, Ettrick, WI (US)

(72) Inventors: Matthew Wayne Kriesel, Melrose, WI (US); Troy Bradley Goodenough, Mindoro, WI (US)

(73) Assignee: Universal Tech Corporation

( * ) Notice: Subject to any disclaimer, the term of this patent is extended or adjusted under 35 U.S.C. 154(b) by 0 days.

This patent is subject to a terminal disclaimer.

(21) Appl. No.: 17/857,152

(22) Filed: Jul. 4, 2022

Related U.S. Application Data

(63) Continuation-in-part of application No. 16/280,849, filed on Feb. 20, 2019, now Pat. No. 11,377,259, which is a continuation-in-part of application No. 15/731,815, filed on Aug. 7, 2017, now Pat. No. 11,124,596, which is a continuation-in-part of application No. 14/999,722, filed on Jun. 20, 2016, now Pat. No. 10,807,767.

(60) Provisional application No. 62/231,004, filed on Jun. 22, 2015.

(51) Int. Cl.
*C08G 18/10* (2006.01)
*C08G 18/36* (2006.01)
*C09J 175/04* (2006.01)

(52) U.S. Cl.
CPC ............ *C08G 18/10* (2013.01); *C08G 18/36* (2013.01); *C09J 175/04* (2013.01); *C08G 2170/40* (2013.01)

(58) Field of Classification Search
CPC .... C08G 18/10; C08G 18/36; C08G 2170/40; C09J 175/04
See application file for complete search history.

(56) References Cited

U.S. PATENT DOCUMENTS

| | | |
|---|---|---|
| 3,507,071 A | 4/1970 | Bryson |
| 5,677,413 A | 10/1997 | Barksby et al. |
| 5,864,001 A | 1/1999 | Masse et al. |
| 6,588,511 B1 | 7/2003 | Kriesel et al. |
| 6,673,409 B1 | 1/2004 | Wheatley |
| 6,896,065 B2 | 5/2005 | Kriesel et al. |
| 7,041,719 B2 | 10/2006 | Wheatley |
| 7,125,602 B2 | 10/2006 | Wheatley |
| 7,252,867 B2 | 8/2007 | Wheatley |
| 7,910,188 B2 | 3/2011 | Wheatley |
| 7,923,088 B2 | 4/2011 | Wheatley |
| 8,110,269 B2 | 2/2012 | Wheatley |
| 8,110,270 B2 | 2/2012 | Wheatley |
| 8,302,213 B2 | 11/2012 | Kriesel |
| 10,807,767 B1 * | 10/2020 | Kriesel ............... A01K 97/06 |
| 11,124,596 B2 * | 9/2021 | Kriesel ............... C09J 191/00 |
| 11,225,358 B2 * | 1/2022 | Kriesel ............... B05D 1/02 |
| 11,505,956 B1 * | 11/2022 | Kriesel ............... A61B 50/22 |
| 2004/0191446 A1 | 9/2004 | Kriesel |
| 2004/0200623 A1 | 10/2004 | Kriesel |
| 2006/0272367 A1 | 12/2006 | Kriesel |
| 2006/0287147 A1 | 12/2006 | Kriesel |
| 2008/0005929 A1 | 1/2008 | Hardy et al. |
| 2008/0026658 A1 | 1/2008 | Kriesel |
| 2008/0250729 A1 | 10/2008 | Kriesel |
| 2009/0042676 A1 | 2/2009 | Kriesel |
| 2010/0170139 A1 | 7/2010 | Zhou |
| 2012/0222457 A1 | 9/2012 | Kriesel et al. |
| 2013/0288060 A1 | 10/2013 | Pind et al. |
| 2013/0296449 A1 | 11/2013 | Peterson et al. |
| 2015/0053583 A1 | 2/2015 | McCormick et al. |

\* cited by examiner

*Primary Examiner* — Rabon A Sergent
(74) *Attorney, Agent, or Firm* — Bryan R. Rosiejka

(57) ABSTRACT

An inventive flexible medical item container comprises a unique adhesive and cohesive viscoelastomeric thermoset polymer. In preferred embodiments, medical items can be repeatedly releasably adhered to and removed from the top side of the container. In addition, the bottom side of the container can be disposed upon and adhered to an object, such as a medical garment, such that the container can be located proximate or adjacent to a medical, dental or hygienic procedure location. In some preferred embodiments, the container further comprises antimicrobial properties. In some preferred embodiments, the container further comprises cleansability properties.

34 Claims, 8 Drawing Sheets

FLEXIBLE MEDICAL ITEM CONTAINER

CROSS-REFERENCE TO RELATED APPLICATION

This application is a Continuation-In-Part of, and claims priority to, U.S. Nonprovisional application Ser. No. 16/280,849 filed Feb. 20, 2019, which is a Continuation-In-Part of U.S. Nonprovisional application Ser. No. 15/731,815 filed Aug. 7, 2017, which is a Continuation-In-Part of U.S. Nonprovisional application Ser. No. 14/999,722 filed Jun. 20, 2016, which is a Nonprovisional application claiming the priority benefit of U.S. Provisional Application No. 62/231,004 filed Jun. 22, 2015, all of which applications are incorporated herein by reference in their entirety.

TECHNICAL FIELD

The present disclosure relates to containers for medical items, such as sterilized or hygienic items utilized during medical, dental and/or hygienic procedures, for example. In some more particular embodiments, the present invention relates to flexible medical item containers comprising a releasably adhesive and cohesive viscoelastomeric thermoset polymer.

BACKGROUND

Medical, dental and other hygienic professionals often utilize conventional hygienic trays (e.g., stainless steel trays) for holding what is generally referred to herein as medical items, such as surgical instruments, dental apparatus, hygienic devices, medications, and the like. Such conventional hygienic trays are typically rigid devices capable of being sterilized, and tend to be constructed of a relatively large horizontal planar base or bottom with comparatively short vertical sidewalls integrated thereupon and an open top. Such design is intended to help prevent medical items disposed therein from falling out of the tray (such as via rolling or sliding off the tray), while also minimizing the vertical barrier presented by the sidewalls to the user (such that a user can attempt to fairly easily access a particular medical item when needed). Unfortunately, despite the sidewalls' relatively minimal vertical presence, users nonetheless inevitably contact the sidewalls during use, thus experiencing blockage to access of the medical items, jarring the tray, or even spilling the medical items and/or the entire tray, any of which result in frustration of the user, a potential need for replacement or re-sterilization of the medical items, increased costs, and/or increased time for a particular medical procedure. Thus, there is a need for a medical item container which has no sidewalls and which can effectively stow medical items while preventing spillage thereof.

In addition, while conventional hygienic trays are in use, the medical items disposed therein are desirably situated in an accessible and orderly manner. However, it can be difficult to consistently maintain the orderliness of such medical items in conventional hygienic trays (typically because the items tend to move around) and to prevent potential cross-contamination of the items. Accordingly, there is also a need for a medical item container that can releasably adhere items thereto.

Furthermore, by their very nature, conventional hygienic trays tend to generally group a variety of medical items at a single location. Unfortunately, this can be rather inconvenient for the ultimate user of such items, particularly if it requires the ultimate user to turn away from the task at hand. For example, surgical room hygienic trays are often provided with a stainless steel top side tray mounted upon a wheeled or legged cabinet-like apparatus. In many instances, the use of conventional hygienic trays actually requires the presence of at least one additional person to whom the ultimate user must first communicate the need for a certain item, then the additional person must provide the item to the user, and finally the user must provide the item back to the additional person (or discard the item) when finished. However, such process can be highly inefficient, and can even lead to the accidental dropping of a particular medical item. As a result, some users (such as in the case of surgeries) may choose to place certain individual medical items at a location proximate to the location of use (e.g., upon a sterilized surgical drape proximate or adjacent to the surgical location) in an attempt to overcome such inefficiencies. However, the individual medical items are still susceptible to movement (e.g., becoming inconveniently located, out-of-reach, etc.), and can easily spill onto the floor or otherwise become unusable (e.g., unsterilized, etc.). Accordingly, there is a need for a medical item container that can be quickly and effectively placed at a location proximate to the location of use. There is also a need for a medical item container that is highly flexible such that it can readily adapt to any surface upon which it is disposed, while effectively and releasably adhering medical items placed thereon, including during disruptive usage conditions.

In addition, conventional hygienic trays are inherently prone to accumulate microbes (e.g., pathogens, airborne microbial contaminants, etc.) and thus require constant attention in order to maintain a sterile environment. Airborne or manually transmitted contaminants deposited upon such trays can remain pathogenically active until subsequently sterilized, such as by periodic antibacterial cleansing, autoclaving, etc. Since there often exists a need to use medical items before such routine pathogenic sterilization occurs, there persistently exists a high risk of pathogenic infection to a patient. To reduce such inadvertent pathogenic contamination, hygienic precautions (e.g., the use of surgical marks, gowns, gloves, etc.) are commonly used to protect against pathogenic contamination. This, however, does not reduce preexisting pathogens already harboring upon a contaminated tray. Accordingly, there is a need for a medical item container which inherently possesses antimicrobial properties, such that it could offer constant pathogenic protection, as opposed to the current practice of persistent pathogenic sterilization safeguards. There may be a further need for a medical item container which could be readily cleaned, such as by washing with water or autoclaving, to restore its full functionality and/or to provide for reuse.

SUMMARY

In response, the invention of the present disclosure solves one or more of the problems and/or needs discussed above. In some embodiments, an inventive flexible medical item container can be in the form of a releasably adhesive, cohesive and antimicrobial polymeric pad or mat, which can be placed at a desired location upon an object, such as a sterilized medical garment for example, preferably at a location that is proximate or adjacent to the location of a medical, dental or hygienic procedure. In other embodiments, an inventive medical item container can be integrated with an object, such as a sterilized medical garment for example, preferably at a predetermined location that is proximate or adjacent to the location of a medical, dental or hygienic procedure.

In some preferred embodiments, an inventive flexible medical item container of the present disclosure for releasably adhering medical items thereto comprises an adhesive and cohesive viscoelastomeric thermoset polymer.

In some aspects, the inventive flexible medical item container further comprises antimicrobial properties. In some further aspects, the inventive flexible medical item container additionally comprises cleansability properties for removing contaminants adhered thereto. In yet further aspects, a cleansing of the inventive flexible medical item container can be conducted via washing with water, wherein such cleansing can fully restore adhesiveness and antimicrobial properties of the inventive flexible medical item container.

In some aspects, no visually detectable amount of polymeric residue will be present upon a medical item adhered to the inventive flexible medical item container upon removal of the medical item from the flexible medical item container. In other aspects, the inventive flexible medical item container further comprises a top side removable protective covering member disposed upon a top side of the flexible medical item container. In yet other aspects, the inventive flexible medical item container is in the form of a prefabricated flexible medical item container.

In some aspects, the inventive flexible medical item container comprises a top side, a bottom side, and a distal edge which forms a periphery about the flexible medical item container. In other aspects, the bottom side can be disposed upon and adhesively adhered to an object via adhesive bonding. In yet other aspects, the inventive flexible medical item container further comprises an additional adhesive component disposed upon the bottom side of the flexible medical item container, wherein the additional adhesive component comprises a greater adhesiveness than the bottom side of the flexible medical item container. In some further aspects, the additional adhesive component comprises a pressure sensitive adhesive. In still other aspects, the inventive flexible medical item container comprises a bottom side removable protective covering member disposed upon the bottom side of the flexible medical item container.

In some aspects, the inventive flexible medical item container comprises a thickness of about 1 mm to about 10 mm.

In some aspects, the adhesive and cohesive viscoelastomeric thermoset polymer of the inventive flexible medical item container is formed from a thermosetting reaction media comprising:
A. about 2 wt % to about 10 wt % isocyanate prepolymer;
B. about 35 wt % to about 75 wt % polyols; and
C. about 10 wt % to about 60 wt % plasticizer;
wherein the polyols comprise about 1 wt % to about 65 wt % straight chain polyols based on the total reaction media weight and about 3 wt % to about 50 wt % crosslinking polyols based on the total reaction media weight; and wherein the plasticizer comprises about 10 wt % to less than about 45 wt % epoxidized triglyceride plasticizer based on the total reaction media weight and 0 wt % to about 40 wt % viscosity reducing plasticizer based on the total reaction media weight. In some further aspects, the isocyanate prepolymer comprises diisocyanate.

In some aspects, the adhesive and cohesive viscoelastomeric thermoset polymer further comprises a straight chain polyol to crosslinking polyol weight ratio of about 3:1 to about 1:3.

In some aspects, the straight chain polyols comprise polyether diol and the crosslinking polyols comprise polyether triol. In other aspects, the epoxidized triglyceride plasticizer comprises epoxidized vegetable oil plasticizer. In yet other aspects, the viscosity reducing plasticizer comprises an ester plasticizer. In still other aspects, the ester plasticizer has a molecular weight of less than about 750. In yet other aspects, the ester plasticizer has a dipole moment of greater than about 1.5 D.

In some aspects, the inventive flexible medical item container further comprises an object, wherein the flexible medical item container is in the form of an integrated flexible medical item container. In some further aspects, the reaction media has been disposed upon a top side of the object while in liquid form, and then allowed to fully cure in-situ to form the adhesive and cohesive viscoelastomeric thermoset polymer. In some further aspects, the inventive flexible medical item container is adhesively adhered to the object via at least adhesive bonding and chemical bonding. In some further aspects, the integrated flexible medical item container comprises a thickness of about 0.5 mm to about 8 mm.

In some aspects, the inventive flexible medical item container comprises an adhesiveness of about 25 gf/cm 2 to about 150 gf/cm 2.

In some preferred embodiments, a method for forming an inventive flexible medical item container for releasably adhering medical items thereto, comprises:
A. providing a reaction media comprising about 2 wt % to about 10 wt % isocyanate prepolymer, about 35 wt % to about 75 wt % polyols comprising about 1 wt % to about 65 wt % straight chain polyols based on the total reaction media weight and about 3 wt % to about 50 wt % crosslinking polyols based on the total reaction media weight, and about 10 wt % to about 60 wt % plasticizer comprising about 10 wt % to less than about 45 wt % epoxidized triglyceride plasticizer based on the total reaction media weight and 0 wt % to about 40 wt % viscosity reducing plasticizer based on the total reaction media weight;
B. providing a suitable mold;
C. disposing the reaction media into the mold while in a liquid state;
D. allowing the reaction media to fully cure into an adhesive and cohesive viscoelastomeric thermoset polymer; and
E. removing the polymer from the mold to provide the inventive flexible medical item container.

In some aspects, the method further comprises disposing medical items upon a top side of the inventive flexible medical item container. In other aspects, the method further comprises disposing a bottom side of the inventive flexible medical item container upon an object. In some further aspects, the method further comprises disposing an additional adhesive component upon the bottom side prior to disposing the inventive flexible medical item container upon the object. In yet other aspects, the isocyanate prepolymer comprises a diisocyanate, the straight chain polyols comprise polyether diol, the crosslinking polyols comprise polyether triol, the epoxidized triglyceride plasticizer comprises epoxidized soybean oil, and the viscosity reducing plasticizer comprises dibutyl sebacate.

In some preferred embodiments, a method for forming an inventive flexible medical item container for releasably adhering medical items thereto, comprises:
A. providing a reaction media comprising about 2 wt % to about 10 wt % isocyanate prepolymer, about 35 wt % to about 75 wt % polyols comprising about 1 wt % to about 65 wt % straight chain polyols based on the total reaction media weight and about 3 wt % to about 50 wt % crosslinking polyols based on the total reaction media weight, and about 10 wt % to about 60 wt % plasticizer comprising about 10 wt % to less than about 45 wt % epoxidized triglyceride plasticizer based on the total reaction media weight and 0 wt % to about 40 wt % viscosity reducing plasticizer based on the total reaction media weight;

B. providing a suitable object;

C. disposing the reaction media upon at least a portion of the object while the reaction media remains in a liquid state; and D. allowing the reaction media to fully cure in-situ into an adhesive and cohesive viscoelastomeric thermoset polymer to provide the inventive flexible medical item container. In some aspects, the method further comprises disposing medical items upon a top side of the inventive flexible medical item container. In other aspects, the isocyanate prepolymer comprises a diisocyanate, wherein the straight chain polyols comprise polyether diol, wherein the crosslinking polyols comprise polyether triol, wherein the epoxidized triglyceride plasticizer comprises epoxidized soybean oil, and wherein the viscosity reducing plasticizer comprises dibutyl sebacate.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

Figure 1:
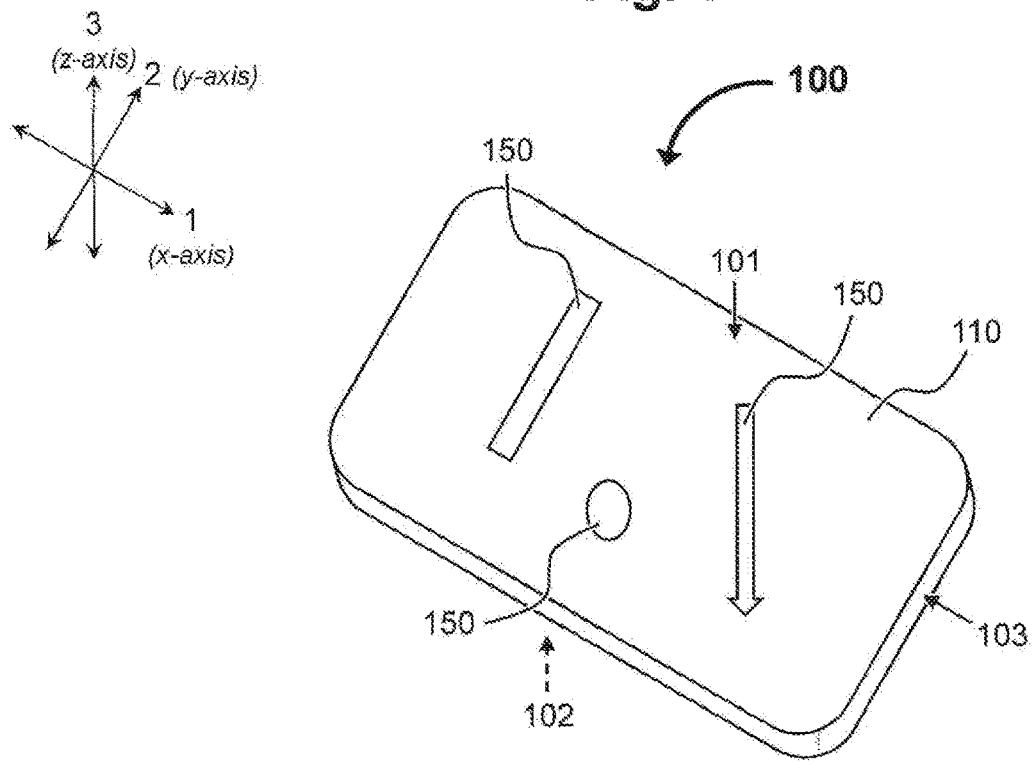
FIG. 1 is a perspective view showing a non-limiting exemplary embodiment of an inventive flexible medical item container of the present disclosure.
Figure 2A:
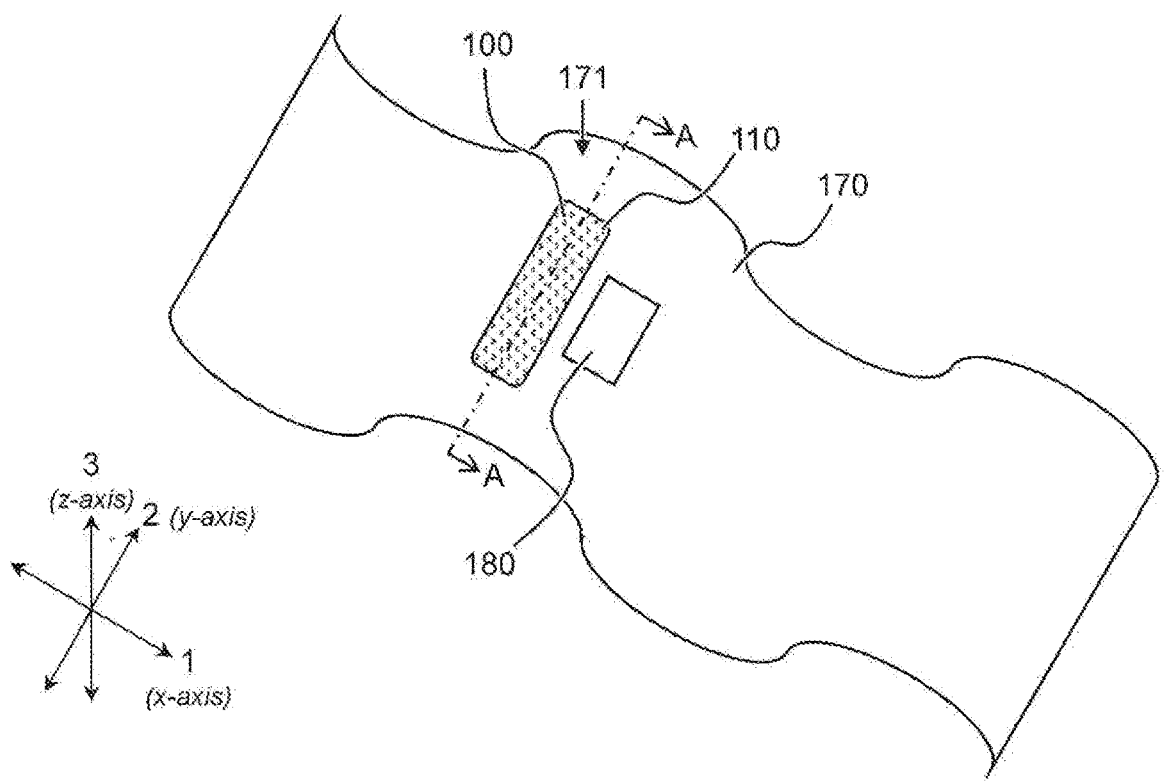
FIG. 2A is a perspective view showing an object in the form of a surgical drape having a surgical opening, wherein a non-limiting exemplary embodiment of an inventive flexible medical item container in a prefabricated form is disposed at a location proximate to the surgical opening.
Figure 2B:
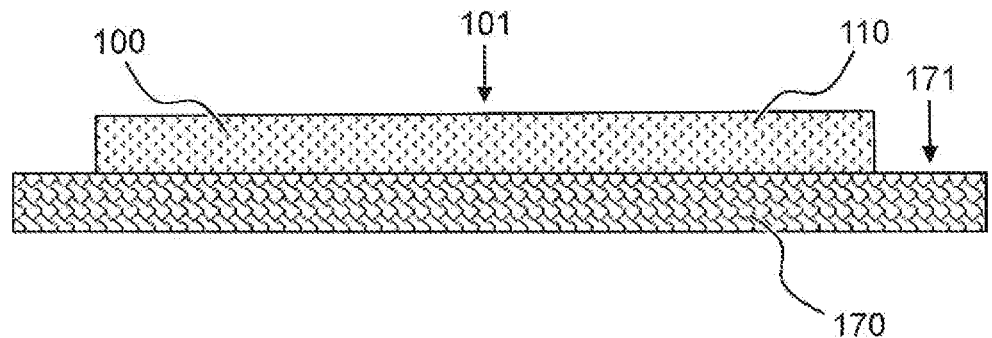
FIG. 2B is a side view showing the flexible medical item container of FIG. 2A as taken along line A-A.

Repeated use of reference characters in the present specification and drawings is intended to represent the same or analogous features or elements of the present invention. It should be understood that the drawings herein are not intended to be drawn to scale, but rather are drawn to show particular elements of the invention.

Test Methods

Adhesiveness & Cohesiveness Test

Figure 8:
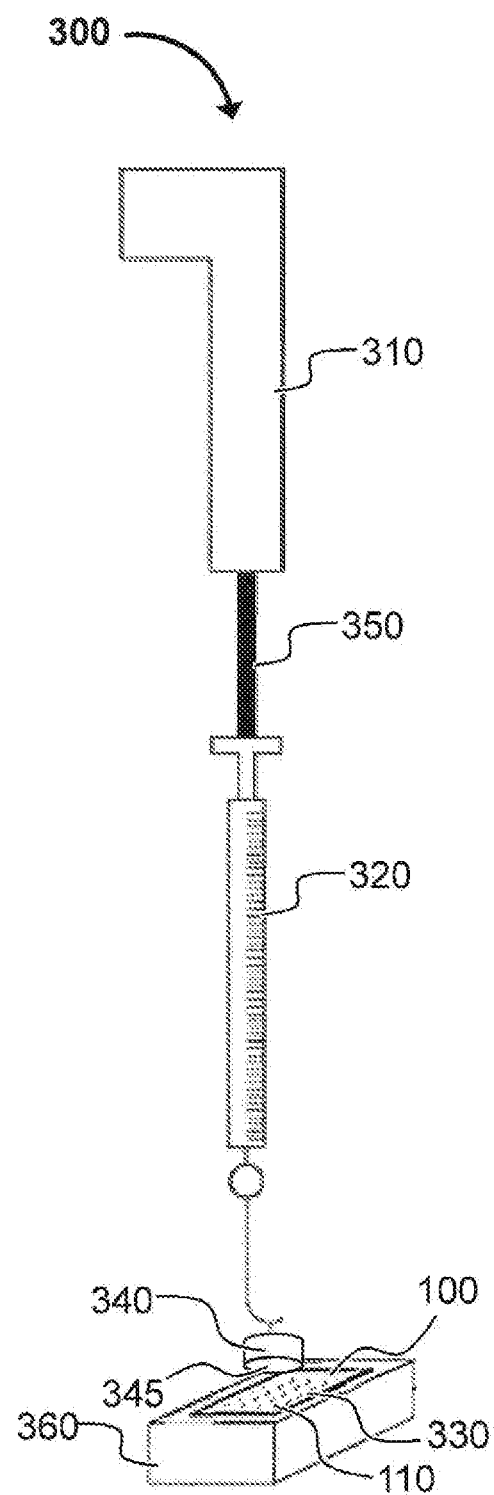
FIG. 8 is a front perspective view showing a testing apparatus for the Adhesiveness & Cohesiveness Test.

Referring to FIG. 8, the illustrated testing apparatus 300 can be utilized for testing the adhesiveness, cohesiveness and releasability properties of various inventive flexible medical item containers 100 and/or adhesive and cohesive viscoelastomeric thermoset polymer 110 components of the present invention. The test apparatus 300 includes a motor driven actuator 310 (similar in concept to that of a standard remote controlled electric garage door opener, such as a Model 3265, available from The Chamberlain Group, Inc., having a place of business located in Elmhurst, Illinois 60126, U.S.A.) or equivalent. The actuator 310 includes a reversible constant speed motor (2.7 cm/sec which is occluded from view) serving to drive a remotely controlled reciprocating test probe 350 connected to a measuring scale 320 to measure adhesiveness, which is the amount of applied force (in grams-force) needed to separate each test sample 330 from a polished nickel cylinder 340 weighing 20.0 grams and having a contact surface area 345 of 1.76 cm 2, thus providing measurements in units of grams-force per square centimeter (gf/cm 2). A testing platform 360 of a laterally movable form is utilized to provide a solid, flat and level surface which allows for repositioning of the test sample 330 to provide accurate repetitions of the test results for each tested sample. Such testing platform 360 should be compatible with the adhesion of the test sample 330 such that it can hold the test sample 330 thereto, and should be of a sufficient weight such that it does not lift from the surface during testing. The testing platform 360 may thus be repositioned to provide a repetition of an untested portion of the test sample 330 for further testing. Accordingly, adhesiveness is measured as the average of ten (10) repetitions upon untested portions of a single test sample 330.

The testing procedure is also useful for determining the cohesiveness of the test sample 330. This is accomplished by visually observing and noting the presence or absence of polymeric residue from test sample 330 upon the test cylinder surface 345 after separating the cylinder 340 from the test sample 330 via the test procedure. The cylinder surface 345 should be cleaned of any residue between each repetition, and the cohesiveness is measured as the average amount of residue over ten (10) repetitions upon untested portions of a single test sample 330.

In addition, additional testing can include the application of pressure to the cylinder 340 when in contact with a test sample 330. By measuring the adhesiveness and cohesiveness of each test sample 330 under differently applied sample application pressures, the adhesive and cohesive effects from applying such different pressures can likewise be determined.

Additionally, adhesiveness changes measured over timed sequence intervals can also be determined so as to provide adhesiveness data upon a test sample's 330 adhesiveness stability. The test procedure can also be utilized to provide adhesiveness data upon short interval adhesiveness increases following an initial adhesive attachment of the cylinder surface 345 to the test sample 330. Differences in adhesiveness between a pressure applied test probe and a non-pressure applied test probe over timed intervals can also be determined.

Figure 3A:
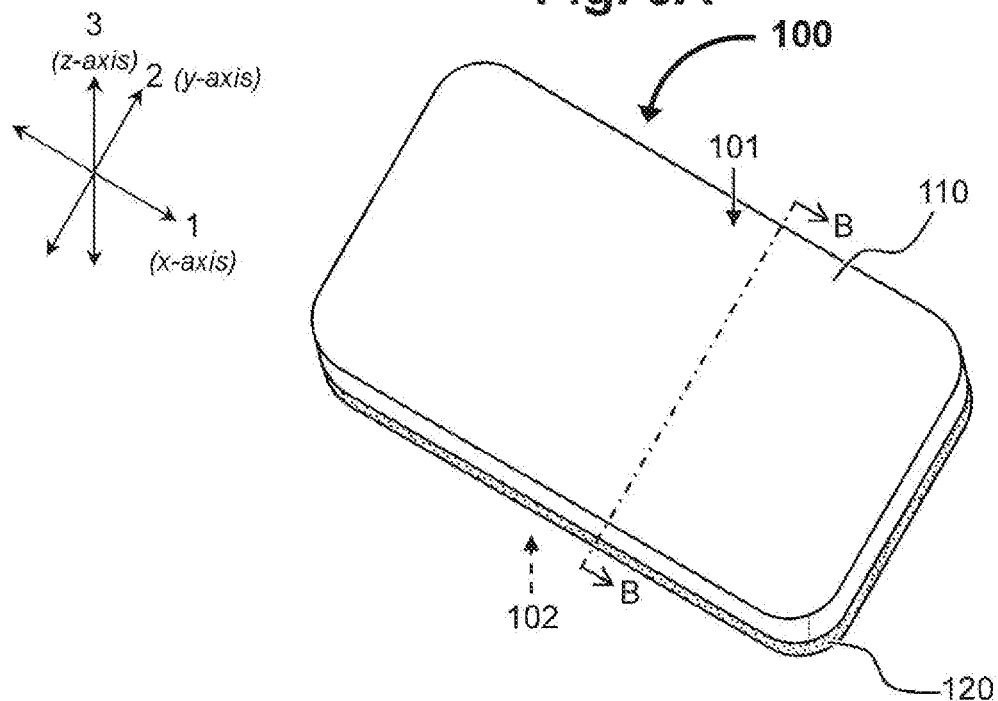
FIG. 3A is a perspective view showing a non-limiting exemplary embodiment of an inventive flexible medical item container of the present disclosure comprising an optional additional adhesive component disposed upon the bottom side of the flexible medical item container.
Figure 3B:
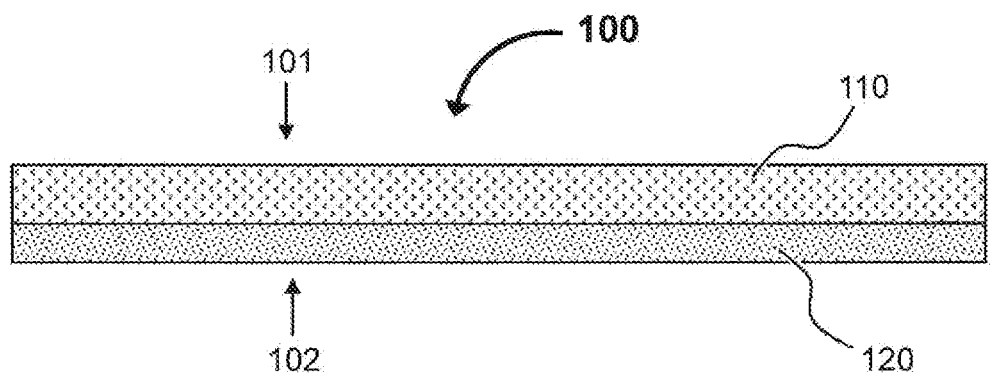
FIG. 3B is a side view showing the flexible medical item container of FIG. 3A as taken along line B-B.

Continuing with FIG. 8, the following more detailed methodology can be utilized to test the adhesiveness and cohesiveness of various test samples 330:

1. Scope
   1.1. This method measures the level of tackiness (adhesiveness) exhibited by adhesive materials and the cohesiveness of such materials, optionally taking into account time dependent and/or pressure dependent adhesiveness properties.
   1.2. This test is designed for use with materials that exhibit adhesive properties, but may also be used with materials not explicitly classified as adhesives, including but not limited to materials having adhesive-like properties.
   1.3. Units—The tested values of adhesiveness are based upon grams-force per square centimeter (gf/cm 2) of the force needed to separate the surface 345 of a polished nickel cylinder 340 having a contact surface area of 1.76 cm 2 from the test sample 330.
2. Terminology
   2.1. As used herein, the term "adhesive-like" refers to having a sticky quality akin to an adhesive, but which derives its sticky quality from a molecular structure that forms a molecular attraction (e.g., rather than adhesive or chemical bonded properties) which is releasable from adhered objects.
   2.2. As used herein, the term "tackiness" refers to the adhesiveness quality of feeling sticky to the touch.
   2.3. As used herein, the term "time dependent adhesive" refers to a material in which adhesive strength changes according to duration of the contact time with a contacting surface.
   2.4. As used herein, the term "pressure sensitive adhesives" refers to a material wherein additional external pressure is required to achieve a change in adhesiveness after initial contact.
3. Summary of Test Method Using the Testing Apparatus Depicted in FIG. 8
   3.1. A test sample 330 is placed upon the top side planar surface of the testing platform 360 and secured thereto.
   3.2. The reciprocating testing probe 350 of the apparatus 300 is lowered to place the surface 345 of the cylinder 340 onto the test sample 330.
   3.3. The surface 345 of the cylinder 340 of the apparatus 300 should remain in contact with the test sample 330 for a designated time period (typically 15 seconds).
   3.4. The cylinder 340 of the apparatus 300 is then raised from the test sample 330 via the reciprocating test probe 350 at a constant speed of 2.7 cm/sec to measure the force in grams required to completely separate the cylinder surface 345 from the test sample 330, as indicated by the measuring scale 320.
   3.5. The measured separating force (adhesiveness) is then calculated and recorded in units of gf/cm 2. In addition, the contacting surface 345 of the cylinder 340 is visually inspected and the amount (e.g., the weight) of residue attached thereto (if any) is recorded to determine cohesiveness. (Note: the surface 345 should be cleaned if residue is present prior to further testing.)
   3.6. Steps 3.1-3.5 are then repeated on untested portions of the test sample 330 so as to obtain a total of ten (10) tests per test sample 330, which are then averaged to yield a final result.
   3.7. Optionally, steps 3.1-3.6 can then be repeated over designated contact time intervals so as to determine time dependent properties of a test sample 330.
   3.8. Optionally, steps 3.1-3.6 can then be repeated over designated applied pressures so as to determine pressure dependent properties of a test sample 330.
4. Apparatus
   4.1. The testing apparatus 300 is illustrated in FIG. 8. Equivalent materials and configurations to those stipulated may be utilized as long as they achieve comparable performance and meet the performance stipulations outlined in Section 4.2 below. Key elements of the apparatus include:
      4.1.1. A reciprocating test probe 350, which is responsible for lowering and raising the cylinder 340 onto the material sample 330 at a constant speed of 2.7 cm/sec.
      4.1.2. The scale 320, which measures the amount of force in grams required to separate the contact surface 345 of the cylinder 340 from the test sample 330.
      4.1.3. The cylinder 340 which weighs 20.0 grams, and the contact surface 345 of the cylinder 340, which is the sole contacting surface with the test sample 330. The contact surface 345 of the cylinder 340 is a circular polished nickel surface having a total contact surface area of 1.76 cm 2.
      4.1.4. The testing platform 360, which provides a solid, level surface for accurate test results and upon which the test sample 330 is secured for testing. This platform 360 is laterally movable so as to allow for repositioning of the test sample 330 for multiple testing.
4.2. Regardless of the specific components used:
   4.2.1. The motor driven actuator 310 must actuate the reciprocating test probe 350 so as to raise and lower the cylinder 340 at a constant speed of 2.70 cm/second.
   4.2.2. The accuracy of the Test, the testing apparatus 300 and scale 320 must measure force in grams with an accuracy resolution of five-percent (5%) or better.
   4.2.3. Except for optional pressure applied tests, a constant pressure of 20.0 grams for the duration of the Test must be applied by the free-hanging, weighted cylinder 340.
4.3. The test procedure is conducted at ambient temperatures of 18° C. to 24° C. and most preferably at 21° C.
5. Calibration
5.1. Prior to first use and at subsequent reasonable testing intervals afterwards, the speed rate of the reciprocating test probe 350 is verified (and adjusted as needed) to ensure consistency within the standard outlined in Section 4.2.1.
5.2. Prior to first use, the accuracy of the scale 320 should be verified against a known weight and adjusted or zeroed accordingly.
6. Procedure
6.1. Assemble the testing apparatus 300.
6.2. Secure a test sample 330 upon the top side planar surface of the testing platform 360, ensuring that the platform 360 does not lift free during testing.
6.3. Lower the free hanging testing cylinder 340 onto the top side of the test sample 330, ensuring even contact between the contact surface 345 and the test sample 330, and ensuring the reciprocating test probe 350 and testing scale 350 are neither pulling nor applying pressure to the cylinder 340.
6.4. Allow the surface 345 of the cylinder 340 to remain in contact with the test sample 330 for 15 seconds or for the duration of another predetermined contact period.
6.5. Continue the test by raising the surface 345 of the cylinder 340 from the test sample 330 until the surface 345 has completely separated from the test sample 330.
6.6. Record the amount of gram-force as measured by the scale 350 required to completely separate the surface 345 of the cylinder 340 from the test sample 330.
6.7. Clean the surface 345 of the cylinder 340 after each iteration with a lint free cloth.
6.8. Reset the scale 350.
6.9. Reposition the testing platform 360 such that a fresh (untested) area of the test sample 330 is tested by the apparatus 300.
6.10. Repeat steps 6.2-6.9 to obtain a total of ten (10) measurements.
6.11. Optionally repeat steps 6.2-6.10 for each duration of testing to determine time dependent properties (e.g., at timed intervals 15 seconds, 30 seconds, 5 minutes, 10 minutes and 15 minutes).
6.12. Optionally repeat steps 6.2-6.10 for each duration of testing to determine pressure dependent properties (by applying incremental predetermined pressures to the cylinder 340).
7. Calculation and Interpretation of Results
7.1. Calculate the adhesiveness for each of the ten (10) test sample 330 measurements by dividing the force (gf) required for the surface 345 of the cylinder 340 to completely detach from the test sample 330 by the contact surface area 345 of the cylinder 740 (1.76 cm 2), and then calculate the average of the ten (10) adhesiveness measurements to establish a final adhesiveness value. The average tested value is given in the amount of grams-force per square centimeter (gf/cm 2) representing the required force to completely separate the surface 345 of the cylinder 340 from the test sample 330, which serves as a measurement of adhesiveness.
7.2. Weigh the amount of residue observed on the surface 345 of the cylinder 340 for each of the ten (10) test repetitions, and then calculate the average of the ten (10) quantities to establish a final average residue weight. Divide the average residue weight by the area of the surface 345 of the cylinder 340 to obtain a cohesiveness value. A lower cohesiveness value is more desirable than a higher value (e.g., wherein a lower value indicates less residue transferred to the contacting surface 345 of the cylinder 340 (i.e., better cohesiveness) than a higher value).
7.3. Repeat steps 7.1 and 7.2 for all iterations tested.

Peel Test

In addition to the Adhesiveness & Cohesiveness Test described above, adhesiveness, cohesiveness and releasability properties can be measured using standardized test methods known to persons having skill in the art, such as ASTM D1876 Peel Resistance of Adhesives (T-Peel Test), as well as other standardized Peel Tests, such as the ASTM 90-Degree Test and ASTM 180-Degree Test, which are used when a flexible material has been bonded to a rigid substrate such as plastic or metal, as well as equivalent tests thereof.

Flexibility Test

The flexibility of an inventive flexible medical item container 100 of the present disclosure, and/or the polymer 110 component thereof, can be tested in accordance with ASTM D4338-97(2021) or equivalent.

Tensile Test

The tensile of an inventive flexible medical item container 100 of the present disclosure, and/or the polymer 110 component thereof, can be tested in accordance with ASTM D3039/D3039M-17 or equivalent.

Definitions

It should be noted that, when employed in the present disclosure, the terms "a" and "an" are intended to mean "at least one" of any stated features, elements, integers, steps, components, or groups and are not intended to be limited to only one of such features, elements, integers, steps, components, or groups thereof, except where specifically stated as such. In addition, use of the phrase "at least one" is not intended to render other uses of the terms "a" or "an" to be limited to only one of a feature, element, integer, step, component, or group.

It should be noted that, when employed in the present disclosure, the terms "comprises," "comprising" and other derivatives from the root term "comprise" are intended to be open ended terms that specify the presence of any stated features, elements, integers, steps, components, or groups, and are not intended to preclude the presence or addition of one or more other features, elements, integers, steps, components, or groups thereof.

As used herein, the terms "adhesive" and "adhesiveness" refer to the bonding strength or adhesive release strength of the inventive flexible medical item container of the present disclosure to another surface. In some embodiments, adhesiveness can be measured by the Adhesiveness & Cohesiveness Test set forth herein.

As used herein, the term "catalytic amount" is a term of the art which is recognized by persons having ordinary skill in the art and refers to an amount that is enough to obtain a desired response or result.

As used herein, the term "coform" refers to a process in which at least one meltblown die head is arranged near a chute through which other materials are added to the web while it is forming. Such other materials may be pulp, cellulose or staple fibers, for example.

As used herein, the terms "cohesive" and "cohesiveness" refer to the ability of the inventive flexible medical item container of the present disclosure to retain its structural integrity when subjected to separating or peeling forces. In some embodiments, cohesiveness can be measured by the Adhesiveness & Cohesiveness Test set forth herein. The cohesive attributes can be further reflected by the separation of a medical item attached to the inventive flexible medical item container without leaving substantially any polymeric residue upon the surface of the medical item, as well as by the flexible medical item container's ability to return to its original innate form upon removal of a medical item attached thereto as prior to attachment of the medical item.

As used herein, the term "effective amount" refers to the amount required to obtain a desired result.

As used herein the term "meltblown" refers to fibers formed by extruding a molten thermoplastic material through a plurality of fine, usually circular, die capillaries as molten threads or filaments into converging high velocity, usually hot, gas (e.g., air) streams that attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Meltblown fibers may be continuous or discontinuous, are generally smaller than 10 microns in average diameter, and are generally tacky when deposited onto the collecting surface.

As used herein with respect to nonwovens, "laminate" and "multilayer laminate" refers to a laminate wherein some of the layers are spunbond or some meltblown such as a spunbond/meltblown/spunbond (SMS) laminate, and others. Such a laminate may be made by sequentially depositing onto a moving forming belt first a spunbond fabric layer, then a meltblown fabric layer and lastly another spunbond layer, and then bonding the laminate. Alternatively, the fabric layers may be made individually, collected in rolls, and combined in a separate bonding step. Such fabrics usually have a basis weight of from about 0.1 osy to about 12 osy (6 gsm to 400 gsm), such as from about 0.75 osy to about 3 osy (25 gsm to 100 gsm). Multilayer laminates may also have various numbers of meltblown layers or multiple spunbond layers in many different configurations and may include other materials like films or coform materials, e.g. SMMS, SM, SFS, etc.

As used herein, the term "nonwoven" refers to a web having a structure of individual fibers or threads that are randomly interlaid, but not in an identifiable manner or pattern as in a woven or knitted fabric.

As used herein, the term "reaction media" refers to an uncured or partially cured mixture of constituents which, upon fully curing, forms the polymer component of the inventive flexible medical item container of the present disclosure.

As used herein, the term "reaction product" refers to the resulting product obtained upon curing a reaction media to form the polymer component of the inventive flexible medical item container of the present disclosure.

As used herein with respect to the inventive flexible medical item container, the terms "releasable" and "releasability" refer to the setting free from restraint or disengagement of a medical item from the inventive flexible medical item container.

As used herein, the term "spunbond" refers to small diameter fibers that are formed by extruding molten thermoplastic material as filaments from a plurality of fine, usually circular capillaries of a spinneret with the diameter of the extruded filaments then being rapidly reduced. Spunbond fibers are generally not tacky when they are deposited onto a collecting surface. Spunbond fibers are generally continuous and have average diameters larger than about 7 microns, such as between about 10 microns and about 20 microns.

As used herein, the terms "viscoelastomeric" and "viscoelastic" are used interchangeably to refer to a substance having viscous and elastic properties.

These terms may be defined with additional language in the remaining portions of the specification.

DETAILED DESCRIPTION

The invention is generally directed to hygienic tray containers, such as those utilized to hold medical items, for example. More specifically, the invention is directed to a unique flexible medical item container comprising an adhesive and cohesive viscoelastomeric thermoset polymer.

Although several exemplary embodiments of the present invention will be described herein, it should be understood that the disclosed embodiments are intended merely as non-limiting examples of the invention that may be embodied in various forms. Therefore, specific details disclosed herein, such as relating to structure, function, and the like, are not to be interpreted as limiting in any manner whatsoever, but rather only as one of numerous example bases for claims and/or teaching persons having ordinary skill in the art to variously employ the present invention in virtually any appropriately detailed structure or circumstance.

Accordingly, in the interest of brevity and conciseness, descriptions herein may be substantially directed to the non-limiting exemplary form of an inventive flexible medical item container comprising a flexible adhesive and cohesive viscoelastic thermoset polymer in the form of a prefabricated pad or mat, for example, which can be placed at a desired location upon an object proximate or adjacent to the location of a medical, dental or hygienic procedure, such as upon a sterilized medical garment, for example, thus presenting a prefabricated flexible medical item container, and in the non-limiting exemplary form of an inventive flexible medical item container comprising an adhesive and cohesive viscoelastic thermoset polymer which has been integrated with an object proximate or adjacent to a predetermined location of a medical, dental or hygienic procedure, such as integrated with a sterilized medical garment, for example, thus presenting an integrated flexible medical item container. As used herein, the term "medical garment" is intended to include medical, dental and other hygienic substrates, typically flexible substrates, including but not limited to, surgical drapes, surgical gowns, scrubs, dental napkins/bibs, hygienic blankets/sheets, and the like.

To gain a better understanding of the present invention, attention is directed to FIGS. 1-8 for exemplary purposes showing a non-limiting embodiment of an inventive flexible medical item container 100 of the present disclosure. As illustrated, the flexible medical item container 100 is shown in the non-limiting exemplary form of being mated with an object 170 in the form of a surgical drape medical garment. However, it should be understood that such objects 170 are not limited to surgical drapes, but rather include any object to which a user desires to dispose the inventive flexible medical item container 100 (e.g., medical garments, tables, bed frames, trays, etc.). Such objects 170 can be rigid, flexible or combinations thereof without departing from the scope of the invention. Accordingly, such objects 170 can comprise any suitable natural or synthetic material that is compatible with (i.e., can suitably adhere to) the adhesive and cohesive viscoelastomeric thermoset polymer 110 component of the inventive flexible medical item container 100. For example, an object 170 can comprise metal, wood, glass, fiberglass, ceramic, concrete, foams, plastics (e.g., polyethylene, polypropylene, etc.), polyesters, nylon, rayon, dacron, manila, polyethylene terephthalate, polyamides, polyurethane, woven textiles, nonwoven substrates, polyacetates, polyacrylics, spandex, latex, orlon, velvet, leather, and a host of other such natural and/or synthetic materials which can suitably support the inventive flexible medical item container 100, as well as combinations thereof. Preferably, such objects 170 can also suitably support the medical items 150 disposed upon inventive flexible medical item container 100. As used herein, the term "medical items" includes any suitable items or instruments utilized in the medical, dental and hygienic fields (e.g., scalpels, scissors, forceps, retractors, saws, needles, staplers, suctions, medications, ultrasounds, scalers, elevators, spreaders, chisels, files, hooks, gauges, wires, threads, bandages, kits, curettes, trocars, scopes, specula, depressors, probes, dilators, markers, clips, tweezers, syringes, nozzles, clamps, jaws, forks, tubes, dishes, bowls, mirrors, drills, excavators, pluggers, burnishers, reamers, broaches, ejectors, pushers, teeth, gags, carvers, bands, retainers, janquets, toothpaste, floss, acupuncture equipment, and the like, and combinations thereof).

In some preferred embodiments, the inventive flexible medical item container 100 can be in the non-limiting form of a pad or mat, for example. In such embodiments, when placed in a laid-flat configuration, the flexible medical item container 100 can comprise a generally planar first or top side 101, and an opposing generally planar second or bottom side 102 distal to the top side 101. The medical item container 100 can further comprise a distal edge(s) or side(s) 103 disposed between and generally orthogonal to the top side 101 and the bottom side 102, which generally forms an outer or exterior perimeter or periphery thereof. Preferably, the bottom side 102 will be disposed upon and adhered to an object 170 during normal use. Such object 170 will generally determine the location of the inventive flexible medical item container 100 during use, and may influence the topographical shape profile of the flexible medical item container 100 as well. Although the inventive flexible medical item container 100 is illustrated to show a generally rectangular shape profile, it should be understood that the container 100 can have any functional shape profile known to persons having ordinary skill in the art (e.g., square, trapezoidal, triangular, circular, ovular, a strip, random, etc.) without departing from the scope of the invention.

Referring now to FIGS. 1-5B, in a first preferred embodiment of the inventive flexible medical item container 100, the invention can be in the form of a prefabricated medical item container 100, which can be disposed onto an object 170 at a location as desired by a user, desirably at a location proximate or adjacent to the location of a particular medical, dental or hygienic procedure. The medical item container 100 can have any suitable dimensions as may be desired for a particular use. For example, in the case of the medical item container 100 having a generally rectangular profile, the medical item container 100 may comprise a length (as measured along the x-axis 1) of about 75 cm and a width (as measured along the y-axis 2) of about 40 cm, such as a length of about 50 cm and a width of about 30 cm, or a length of about 40 cm and a width of about 25 cm, or other desired dimensions for a particular use. The inventive flexible medical item container 100 can also comprise a height or thickness (as measured along the z-axis 3). There are no particular limits to the thickness. In the case of a prefabricated medical item container 100, the thickness will typically range from about 1 mm to about 10 mm, such as from about 2 mm to about 5 mm. It should be understood that the thickness can be less than 1 mm or greater than 10 mm for a prefabricated medical item container 100 without departing from the scope of the invention, but such extra thickness generally does not add any benefit to the invention. In addition, it should be understood that the thickness can be uniform or non-uniform without departing from the scope of the invention.

In some preferred aspects, the medical item container 100 is viscoelastomeric and flexible, and more preferably highly flexible (as opposed to rigid or semi-rigid). Such flexibility is a function of the unique adhesive and cohesive viscoelastic thermoset polymer 110 of which the medical item container 100 is comprised. As a result, the inventive flexible medical item container 100 can be securely utilized with, and will conform to, virtually any solid object 170 (e.g., rigid, semi-rigid, semi-flexible, highly flexible, etc.) upon which it is disposed, including but not limited to, flexible woven textile materials and flexible nonwoven materials (e.g., spunbond, meltblown, coform, bonded-carded-web, laminates such as spunbond/meltblown/spunbond (SMS), etc.). This provides a significant advantage over conventional hygienic trays, since the inventive flexible medical item container 100 can be placed proximate or adjacent to the location of a particular medical, dental or hygienic procedure. For example, the inventive flexible medical item container 100 can be disposed upon an object 170 in the form of a flexible nonwoven surgical drape at a location proximate to a surgery access opening 180 of the surgical drape (see e.g., FIG. 2). Furthermore, the inventive flexible medical item container 100 solves the age-old problem of medical instruments being inconveniently located with respect to the user, typically such that an additional person is often required to provide such medical instruments to the user during use thereof.

Continuing with FIG. 1, and with additional reference to FIGS. 2A-3B and FIG. 8, in some preferred aspects, the inventive flexible medical item container 100 comprises adhesive properties, preferably throughout its entire exterior surface. As a result, not only can the bottom side 102 of the medical item container 100 be disposed upon and adhered to an object 170, but in addition one or more various medical instruments 150 can also be releasably adhered to the top side 101 of the flexible medical item container 100. Such adhesive properties are a function of the unique adhesive and cohesive viscoelastic thermoset polymer 110 of which the medical item container 100 is comprised. There is no particular limit to the adhesion strength (i.e., adhesiveness) of the medical item container 100, provided however that the container 100 can securely adhere a medical item 150 disposed thereon and a user can effectively release a particular medical item 150 that has been attached or reattached (e.g., after subsequent uses) thereon when such medical item 150 is needed. It has been discovered herein that a suitable adhesiveness of the inventive flexible medical item container 100 will typically range from about 25 grams-force per square centimeter (gf/cm 2) to about 150 gf/cm 2, such as about 40 gf/cm 2 to about 100 gf/cm 2, for improved benefits, as measured by the Adhesiveness & Cohesiveness Test. Such adhesiveness properties provide a significant advantage over conventional hygienic trays, which are not adhesive, since the inventive flexible medical item container 100 (and thus the medical items 150 disposed thereon) can be conveniently placed proximate or adjacent to the location of a particular medical, dental or hygienic procedure. For example, the inventive flexible medical item container 100 can be disposed upon an object 170 in the form of a flexible nonwoven surgical drape at a location proximate to a surgery access opening 180 of the surgical drape (see e.g., FIG. 2A). The inventive flexible medical item container 100 also helps solve the age-old problem of medical items 150 being accidentally spilled or dropped onto the floor (such as when handing off from an additional person to the user) since the user can now securely attach or reattach such medical items 150 at or near the site of a procedure within convenient reach of the user.

As referenced above, in some preferred aspects, the adhesiveness of the inventive flexible medical item container 100 can be formulated to be about 25 gf/cm 2 to about 150 gf/cm 2, as measured by the Adhesiveness & Cohesiveness Test. Such adhesiveness range has been found herein to ideal for the suitable attachment, release and subsequent reattachment of most common medical items 150. However, it should be understood that the flexible medical item container 100 can have an adhesiveness of less than 25 gf/cm 2 or greater than 150 gf/cm 2 without departing from the scope of the invention. Nonetheless, in some instances, such preferred adhesiveness values may be considered relatively low with respect to attachment of the flexible medical item container 100 to an object 170. Generally, the flexible medical item container 100 will remain securely adhered to an object 170 while a medical item 150 is removed (i.e., released) therefrom, since the amount of container 100 area in contact with an object 170 (i.e., typically the entire bottom side 102) is typically greater than the amount of area of any single medical item 150 that is in contact with the top side 101 of the container 100. However, certain relatively large size medical items 150 and/or certain less adhesively compatible object 170 surfaces may result in potential detachment of at least a portion of the container 100 when removing such medical items 150 therefrom. Thus, it may be desirable to dispose an optional adhesive component 120 upon the bottom side 102 of the medical item container 100 to alleviate the potential occurrence of such detachment (see e.g., FIGS. 3A-3B). Suitable optional adhesive components 120 should be adhesively compatible with both the flexible medical item container 100 and the object 170, and include those known to persons having ordinary skill in the art. Preferably, the optional adhesive component 120 will exhibit a final adhesiveness that is greater than the adhesiveness of the flexible medical item container 100, such as an adhesiveness of at least about 200 gf/cm 2 as measured by the Adhesiveness & Cohesiveness Test (wherein the additional adhesive component 120 serves as the test sample 330), such as at least about 1,000 gf/cm 2, or at least about 2,000 gf/cm 2, or greater, to provide additional benefits. In some desirable aspects, a pressure sensitive additional adhesive component 120 can be particularly suitable for use with the inventive flexible medical item container 100. For example, one suitable additional adhesive component 120 is 3M QUICK BONDING ADHESIVE 360 (such as associated with 3M ADHESIVE TRANSFER TAPE 9627), which is a pressure sensitive adhesive available from 3M Company, having a place of business located in St. Paul, Minnesota, USA. Such optional adhesive component 120 can preferably be applied to the bottom side of the medical item container 100, such as a generally continuous layer, or in a discontinuous manner, without departing from the scope of the invention.

Continuing now with FIGS. 1-2B and FIG. 8, in some preferred aspects, the inventive flexible medical item container 100 comprises excellent cohesiveness properties, thus allowing the medical item container 100 to remain fully functional throughout an entire medical, dental or hygienic procedure, and potentially beyond such use. Such cohesiveness properties are a function of the unique adhesive and cohesive viscoelastic thermoset polymer 110 of which the medical item container 100 is comprised. For instance, despite being viscoelastomeric, flexible and releasably adhesive, the medical item container 100 will return to its original innate state after removing a medical item 150 from the top side 101 of the container 100 (which is accomplished by a user exerting an opposing or counteracting force upon the medical item 150 which overcomes the adhesion force of the container 100). Accordingly, the inventive medical item container 100 will substantially return to the same overall shape profile it had prior to disposing a medical item 150 upon it, despite any deformation of the container 100 during such removal, such as due to the application of external forces. In addition, such cohesiveness substantially prevents separation of the inventive flexible medical item container 100 from itself (i.e., transference of polymer to a medical item 150) upon removal of medical items 150 attached thereto. Accordingly, the medical item container 100 will leave no visually detectable polymeric residue on a medical item 150 upon being removed from medical item container 100, such as measured by the Adhesiveness & Cohesiveness Test, and more preferably no polymeric residue whatsoever. Such cohesiveness properties provide a significant advantage over conventional adhesives, which tend to change form and weaken after each use and/or which tend leave residue upon the contacting surface of items removed therefrom.

In some preferred aspects, the inventive flexible medical item container 100 comprises unique antimicrobial properties, including antipathogenic properties. In other words, the inventive medical item container 100 can neutralize microbial pathogens (e.g., viruses, bacteria, germs, etc.) which may be present upon anything that comes into contact with the container 100, including the engaged surfaces of medical items 150, gloved hands, etc. Such antimicrobial properties are a function of the unique adhesive and cohesive viscoelastic thermoset polymer 110 of which the flexible medical item container 100 is comprised, and presents an important attribute of a container 100 utilized with medical items 150, and intended for use in a hygienic or sterilized environment. Furthermore, the antimicrobial properties of the inventive flexible medical item container 100 remain active throughout the container's use, and beyond. Such antimicrobial properties provide a significant advantage over conventional hygienic trays which typically do not exhibit such antimicrobial properties, and solves the age-old problem of the continuously required cleaning and re-sterilization of conventional hygienic trays and medical items 150 (such as by autoclaving) during a medical, dental or hygienic procedure.

Figure 4A:
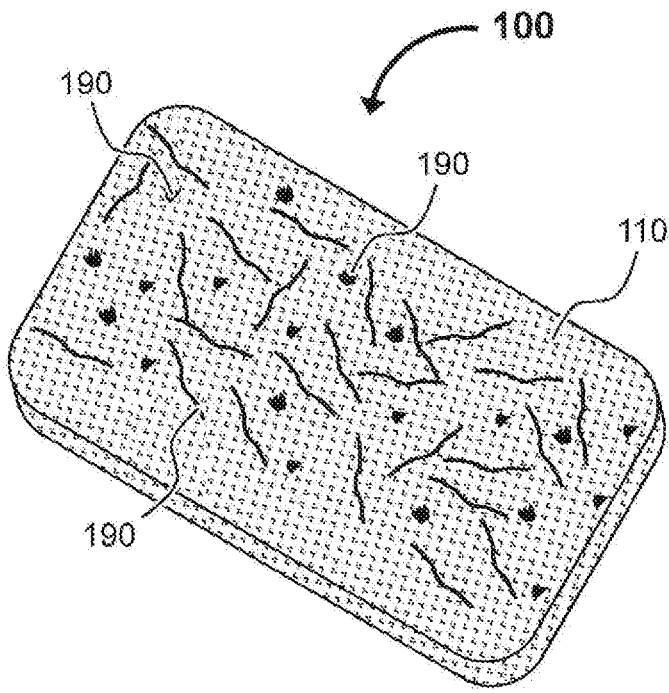
FIG. 4A is a perspective view showing a non-limiting exemplary embodiment of an inventive flexible medical item container of the present disclosure having contaminants disposed thereon.
Figure 4B:
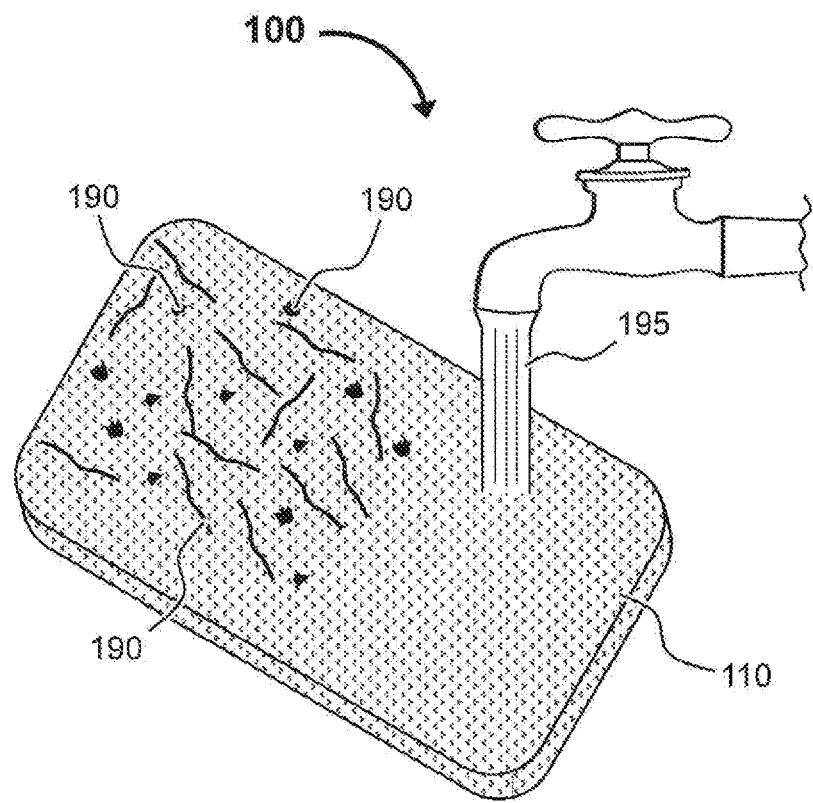
FIG. 4B is a perspective view showing the inventive flexible medical item container of FIG. 4A while in the process of being cleansed with water to remove the contaminants therefrom.
Figure 4C:
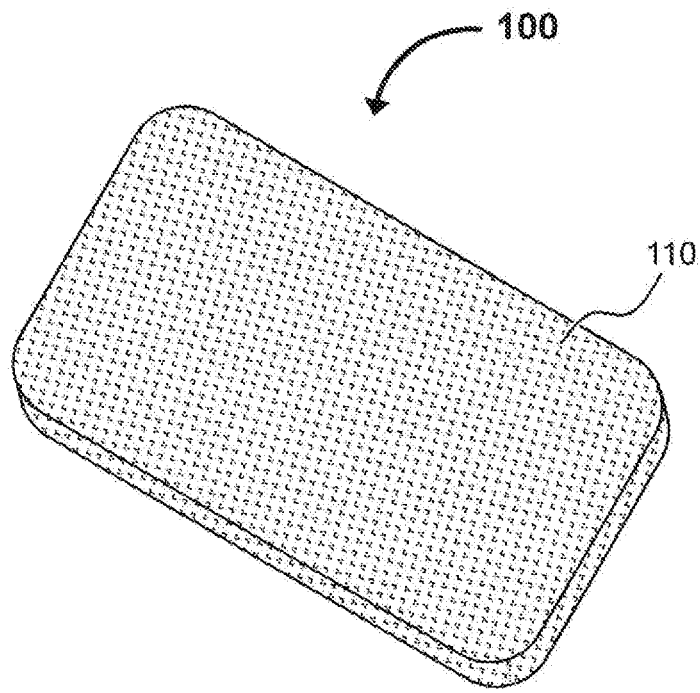
FIG. 4C is a top view of the inventive flexible medical item container of FIG. 4B after being cleansed and restored to its original state.

Referring now to FIGS. 4A-4C, in some preferred aspects, the inventive flexible medical item container 100 comprises unique cleansability properties. Such cleansability properties are a function of the unique adhesive and cohesive viscoelastic thermoset polymer 110 of which the flexible medical item container 100 is comprised. For example, due to its adhesive nature, the inventive container 100 can potentially adhesively attract contaminants 190, such as airborne contaminants (e.g., dust, lint, debris, etc.) and/or patient derived contaminants (e.g., blood, saliva, hair, keratinocytes, etc.), which can potentially diminish adhesiveness and/or antimicrobial properties over time (typically by reducing the available exposed area of the container 100). However, the original adhesiveness and antimicrobial properties of the inventive flexible medical item container 100 can be easily restored via conventional washing and/or other suitable contaminant removal techniques (e.g., autoclaving). For example, unlike conventional adhesive products which must be discarded upon contamination (typically after merely a single use), the inventive flexible medical item container 100 can be cleansed from contaminants and restored to its substantially original adhesive and antimicrobial efficacy. Surprisingly, conventional washing with water 195 or with a solution of water and common soap, such as DAWN dish detergent, available from Procter & Gamble, having a place of business located in Cincinnati, Ohio, USA 45202 (e.g., rinsing, hand-washing, scrubbing, washing machines, dishwashers, etc.), as well as autoclaving (i.e., applying high pressure steam), may be effectively utilized to eradicate and remove contaminants 190 therefrom and thereby permit fully functional re-use of the cleansed inventive flexible medical item container 100. Accordingly, the inventive flexible medical item container 100 is environmentally friendly, and may be considered as "green" technology. This provides yet another significant advantage over conventional adhesive products (which typically do not exhibit such cleansability and reusability capabilities).

Figure 5A:
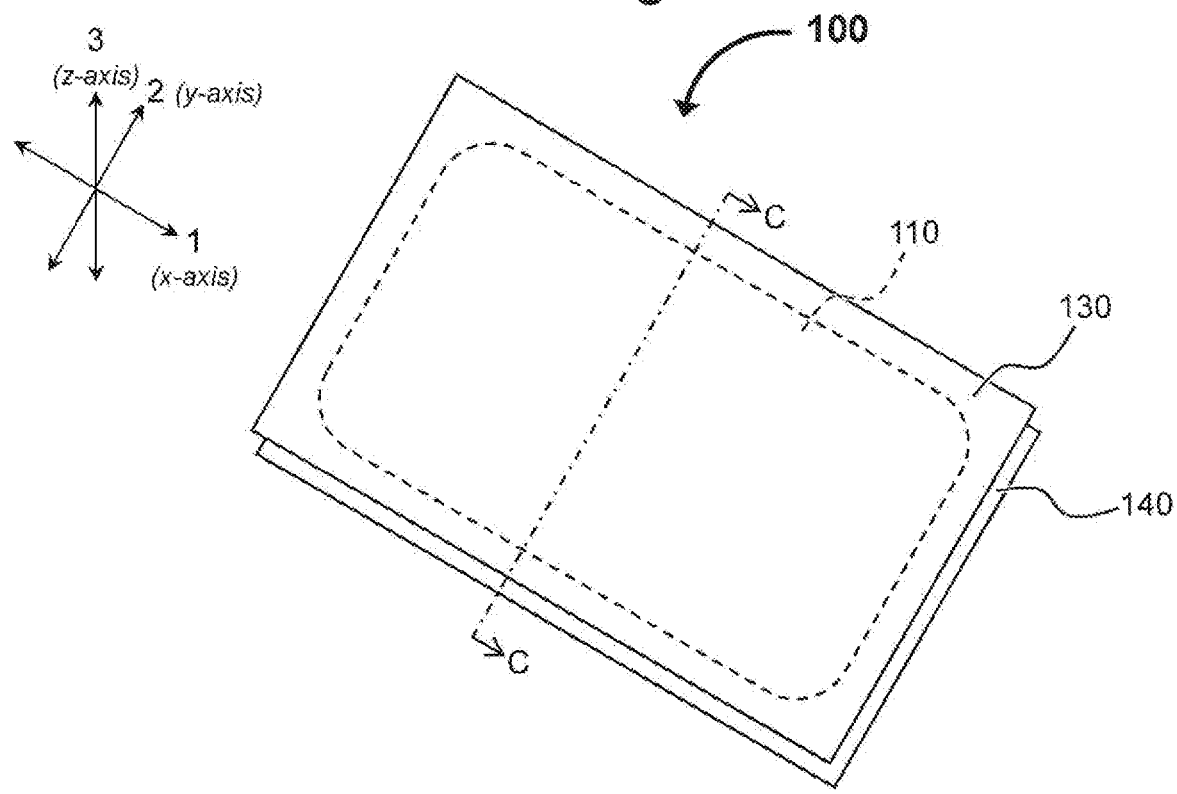
FIG. 5A is a perspective view showing a non-limiting exemplary embodiment of an inventive flexible medical item container comprising an optional top side removable protective covering member and an optional bottom side removable protective covering member.
Figure 5B:
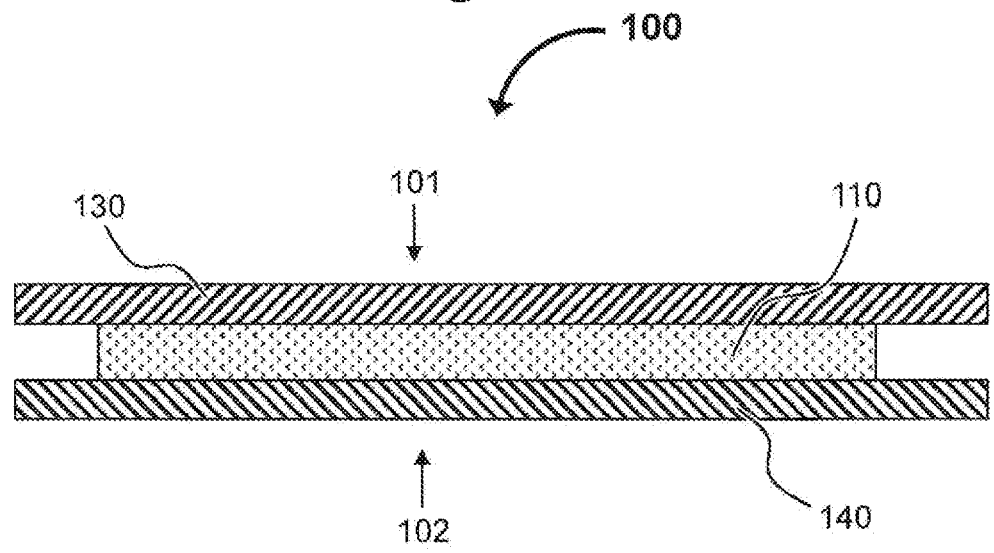
FIG. 5B is a side view showing the flexible medical item container of FIG. 5A as taken along line C-C.

Referring now to FIGS. 5A-5B, in some aspects, due to at least the inventive flexible medical item container's 100 inherently adhesive nature, as well as its intended use in hygienic or sterilized environment, it may be desirable to dispose an optional top side removable protective covering member 130 upon the top side 101 of the container 100 and/or an optional bottom side removable protective covering member 140 upon the bottom side 102 of the container 100. For example, such protective covering members 130, 140 can allow for effective shipment of the container 100, ease of handling the container 100 (e.g., preventing the container 100 from adhering to a user's hands), and can prevent undesired contamination of the container 100 by contaminants 190 prior to its intended use. In some aspects, such protective covering members 130,140 can also be useful as packaging materials for the invention. Such protective covering members 130,140 can comprise any suitable material which can be completely (and preferably relatively easily) removed from the container 100 without leaving any covering materials upon the container 100 upon removal. For example, materials which have a relatively low or incompatible adhesive affinity to the flexible medical item container 100 can be used with the invention to provide suitable protective covering members 130,140 for the exposed top side 101 and/or bottom side 102 surfaces, respectfully, of the container 100. In aspects where the bottom side 102 comprises an optional additional adhesive component 120, the bottom side removable protective covering member 140 can preferably comprise suitable materials which can be completely (and preferably relatively easily) removed from the additional adhesive component 120 without leaving any covering materials upon the bottom side 102 of the container 100 upon removal. Examples of suitable protective covering members 130,140 can include, but are not limited to, silicone-coated substrates, polyvinyl chloride (PVC) films, paraffin-coated substrates, TEFLON-coated substrates, and the like, which tend to be less adhesively compatible with the inventive container 100 (as well as with most additional adhesive components 120) than most other materials.

Figure 6A:
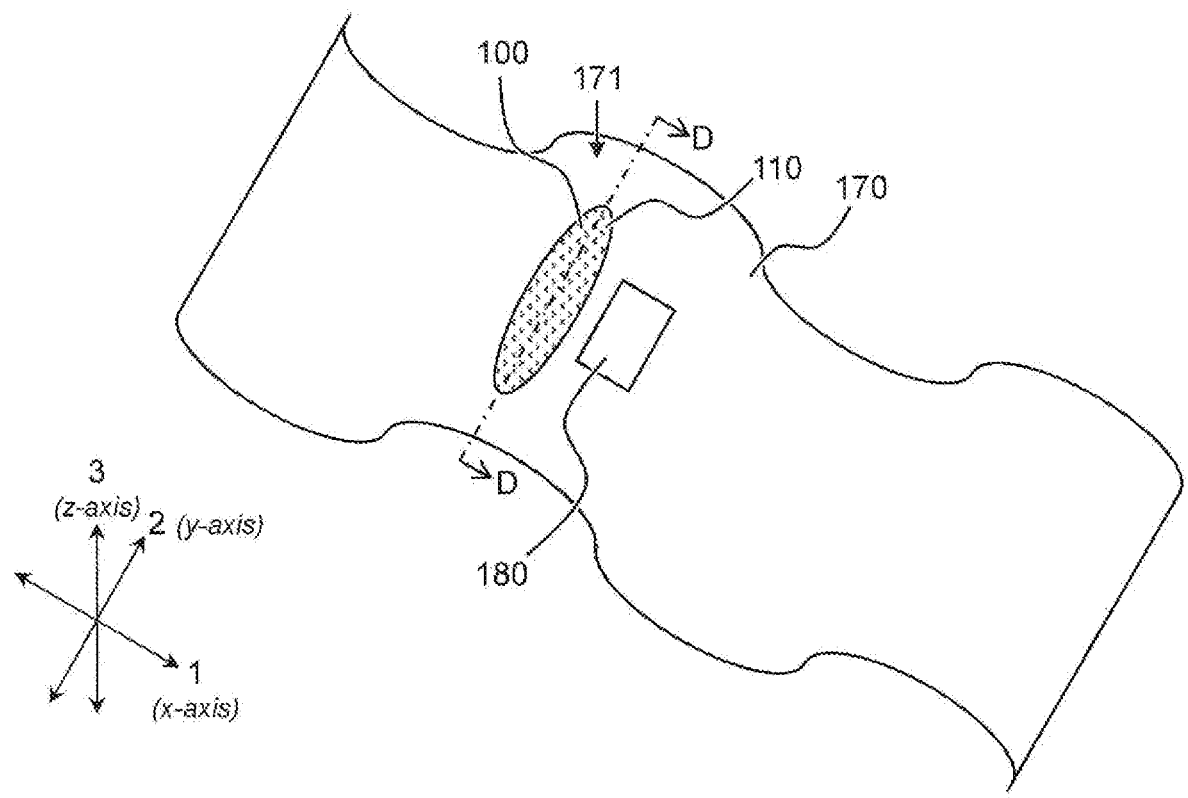
FIG. 6A is a perspective view showing an object in the form of a surgical drape having a surgical opening, wherein a non-limiting exemplary embodiment of an inventive flexible medical item container formed in-situ is disposed at a location proximate to the surgical opening.
Figure 6B:
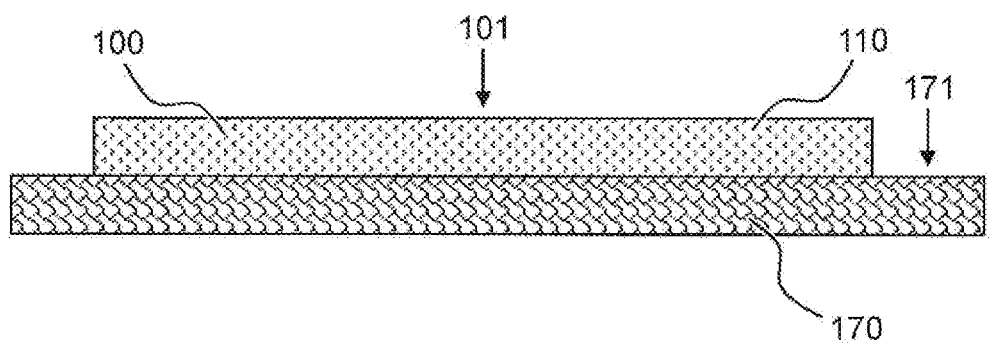
FIG. 6B is a side view showing the flexible medical item container of FIG. 6A as taken along line D-D, wherein the polymer component is disposed upon the top side of the object.

Referring now to FIGS. 1 and 6A-6B, as referenced above, the inventive flexible medical item container 100 comprises a unique adhesive and cohesive viscoelastomeric thermoset polymer 110. The polymer 110 can typically be formed via the preparation and subsequent curing of a thermosetting reaction media. In some preferred embodiments, the reaction media comprises (based on the total reaction media weight) about 2 percent by weight (wt %) to about 10 wt % isocyanate prepolymer, about 35 wt % to about 75 wt % polyols comprising about 1 wt % to about 65 wt % (based on the total reaction media weight) straight chain linking polyols and about 3 wt % to about 50 wt % (based on the total reaction media weight) crosslinking polyols, and about 10 wt % to about 60 wt % plasticizer comprising about 10 wt % to less than about 45 wt % (based on the total reaction media weight) epoxidized triglyceride plasticizer and about 0 wt % to about 40 wt % (based on the total reaction media weight) viscosity reducing plasticizer, preferably an ester plasticizer. Desirably, the polymer 110 is formed from a substantially uniform admixture of the reaction media constituents.

It has been discovered herein that the reaction media and the resulting polymer 110 are substantially free from VOC's. It has been further discovered herein that the weight of the reaction media and the weight of the resulting polymer 110 (i.e., upon curing the reaction media) remain substantially constant. Thus, the "wt %" values of each component referenced above can alternatively be expressed in terms of total "polymer" weight, without departing from the scope of the invention. Accordingly, in some preferred embodiments, the adhesive and cohesive viscoelastomeric thermoset polymer 110 comprises (based on the total polymer weight) about 2 wt % to about 10 wt % isocyanate prepolymer, about 35 wt % to about 75 wt % polyols comprising about 1 wt % to about 65 wt % (based on the total polymer weight) straight chain linking polyols and about 3 wt % to about 50 wt % (based on the total polymer weight) crosslinking polyols, and about 10 wt % to about 60 wt % total plasticizer comprising about 10 wt % to less than about 45 wt % (based on the total polymer weight) epoxidized triglyceride plasticizer and about 0 wt % to about 40 wt % (based on the total polymer weight) viscosity reducing plasticizer, preferably an ester plasticizer. Of course, it should be understood that when expressing the components in terms of wt % based on total "polymer" weight, such components have actually been combined and reacted to form the polymer thereof. In the interest of brevity, the "wt %" of the polymer constituents will typically be expressed in terms of total reaction media weight herein.

In some embodiments, the straight chain polyols and the crosslinking polyols can each comprise repetitive oxygen groups. In other embodiments, the straight chain polyols and the crosslinking polyols can each comprise repetitive ether groups. In still other embodiments, the straight chain polyols and the crosslinking polyols can each comprise hydroxyl groups, desirably wherein two (2) of the hydroxyl groups are terminal hydroxyl groups. In some preferred embodiments, the straight chain polyols and the crosslinking polyols can each comprise a polyether having a molecular weight of about 1,000 to about 20,000. In some embodiments, the straight chain polyols and crosslinking polyols can be present in a straight chain polyol to crosslinking polyol weight ratio of about 1:3 to about 3:1.

In some preferred embodiments, the plasticizer is uniformly dispersed and cohesively bound throughout the polymeric infrastructure of the polymer 110. In some embodiments, the polymer 110 can comprise an epoxidized triglyceride plasticizer to viscosity reducing plasticizer weight ratio of 1:0 to about 1:3.

The adhesive and cohesive viscoelastomeric thermoset polymer 110 of the present invention is particularly well suited for use with the inventive flexible medical item container 100, such as the non-limiting exemplary embodiments described herein. As referenced above, such unique polymer 110 can comprise an isocyanate prepolymer, polyols in the form of straight chain polyols (e.g., diols) and crosslinking polyols (e.g., triols or higher), and select plasticizers. The isocyanate prepolymer in combination with prescribed amounts of straight chain polyols and crosslinking polyols provides a thermoset infrastructure for effectively housing the plasticizer(s) in a form which unexpectedly contributes to the unique viscoelastomeric, cohesiveness, adhesiveness, releasability, cleansability, reusability and antimicrobial features of the inventive flexible medical item container 100. Furthermore, the unexpected cohesiveness attributes of the polymer 110 provides for a stabilized polymer which exhibits substantially no plasticizer leakage (also referred to as "bleeding") despite the relatively high plasticizer content (i.e., about 10 wt % or greater).

As referenced above, the adhesive and cohesive viscoelastomeric thermoset polymer 110 can be derived from a thermosetting reaction media comprised of a substantially uniform admixture of an isocyanate prepolymer, prescribed amounts of polyols (e.g., polyether diols and polyether triols) and a carefully controlled amount of select plasticizers. The isocyanate prepolymer in combination with a controlled amount of polyols in the form of straight chain polyols (preferably diols) and crosslinking polyols (preferably crosslinking triols) provides a thermoset infrastructure for effectively housing the plasticizing components in a form which unexpectedly contributes to the unique stabilized, viscoelastic, adhesive, cohesive, releasability and antimicrobial attributes of the flexible medical item container 100, while also permitting a restorative cleansability function via conventional washing and/or autoclaving techniques. Accordingly, the unexpected cohesiveness attributes of the viscoelastic thermoset polymer 110 substantially prevent plasticizer leakage from the flexible medical item container 100, which solves a long-standing problem of existing polymers having high plasticizer loadings (i.e., greater than about 10 wt % of the total reaction media weight).

A highly effective thermosetting reaction media for preparing the adhesive and cohesive viscoelastomeric thermoset polymer 110 of the present disclosure comprises a prepolymer, polyols and plasticizer. More particularly, the reaction media comprises (i) a prepolymer, such as an isocyanate prepolymer (e.g., a polyol reacted with an isocyanate), more preferably a diisocyanate prepolymer (e.g., methylene diphenyl diisocyanate (MDI)), ranging from about 2 wt % to about 10 wt % of the total reaction media weight; (ii) polyols, ranging from about 35 wt % to about 75 wt % of the total reaction media weight, wherein the polyols include straight chain linking polyols (preferably diols) and crosslinking polyols (preferably triols); and (iii) plasticizer, ranging from about 10 wt % to about 60 wt % of the total reaction media weight, wherein the plasticizer includes an epoxidized triglyceride plasticizer in an amount of about 10 wt % to less than about 50 wt % of the total reaction media weight, such as about 10 wt % to about 45 wt % of the total reaction media, or about 10 wt % to less than 45 wt % of the total reaction media weight to provide improved benefits, and optionally a reaction media viscosity-reducing plasticizer, preferably an ester plasticizer, in an amount of about 0 wt % to about 40 wt % of the total reaction media weight. The viscoelastomeric thermoset polymer 110 can also optionally comprise additional components including, but not limited to, additional plasticizers, catalysts, initiators, colorants (e.g., dyes), UV inhibitors, antioxidants, and the like, as would be known to persons having ordinary skill in the art, without departing from the scope of the invention. As referenced above, it has been observed herein that the weight of the reaction media and the weight of the resulting reaction product (i.e., the polymer 110) remains substantially equivalent upon mixing and curing the reaction media; thus, the compositional amount (i.e., wt %) of each constituent may be expressed in terms of "wt % by weight of the polymer" without departing from the scope of the invention.

As referenced above, the thermosetting reaction media (and thus the resulting polymer 110) comprises a quantity of prepolymer which forms the backbone of the polymer 110. Such prepolymer will typically be present in an amount of about 2 wt % to about 10 wt % of the total reaction media weight, such as about 3 wt % to about 9 wt %, or about 4 wt % to about 8 wt % of the total reaction media weight to provide improved benefits. Suitable prepolymers can include a ring-opening species of a hardener (e.g., amines, amides, mercaptans, anhydrides, isocyanates including polyisocyanates (such as a diisocyanate), etc.). Suitable polyisocyanates include, but are not limited to, aromatic diisocyanates (e.g., diphenylmethane diisocyanate, methylene diphenyl diisocyanate (MDI), toluene diisocyanate (TDI), etc.) and aliphatic diisocyanates (e.g., hexamethylene diisocyanate (HDI), isophorone diisocyanate (IPDI), etc.) in a conventional prepolymer form. In one non-limiting example, a methylene diphenyl diisocyanate (MDI) designated as ELASTOCAST TQZ-P23, available from BASF Corporation, having a place of business located in Florham Park, New Jersey, USA, can provide a suitable prepolymer to form the viscoelastomeric thermoset polymer 110 component of the inventive flexible medical item container 100.

The thermosetting reaction media (and thus the resulting polymer 110) also comprises a quantity of polyols, typically ranging from about 35 wt % to about 75 wt % of the total reaction media weight, such as about 38 wt % to about 65 wt %, or about 40 wt % to about 55 wt % of the total reaction media weight, to provide improved benefits. More particularly, the polyols include straight chain polyols and crosslinking polyols. In some desirable aspects, the straight chain polyols can be in the form of diols (e.g., a diol having two terminal reactive groups), and the crosslinking polyols can be in the form of triols (e.g., having two terminal reactive groups and one additional reactive group). In such aspects, the diol and triol components of the reaction media are typically liquid at room temperature (i.e., about 21° C.) and generally have a molecular weight of about 1,000 to about 20,000, such as about 1,000 to about 15,000, or about 1,000 to about 10,000, to provide improved benefits. The adhesiveness and cohesiveness of the resulting polymer 110 depend upon using a controlled polyol balance within the thermosetting reaction media. It has been discovered herein that the amount of diols and triols (preferably reacted in the presence of an effective amount of plasticizer within the reaction media) can suitably fall within a prescribed diol to triol weight ratio of about 1:3 to about 3:1, such as about 1:2 to 2:1, or about 7:13 to about 13:7, to provide the desired viscoelastic, adhesive, cohesive, releasability, cleansability, and/or antimicrobial (including antipathogenic) attributes for effective use herein (while also inhibiting bleeding of plasticizer from the polymer 110). The content and type of polyols can have a pronounced effect upon imparting the necessary thermoset polymeric infrastructure for obtaining the polymer 110 attributes herein. Accordingly, it has been discovered herein that when the weight ratio of diols to triols deviates outside a range of about 1:3 to about 3:1, the desired adhesiveness, cohesiveness and releasability attributes of the resultant polymer 110 will begin to diminish. Thus, a controlled balance within the cited ranges with respect to the straight chain diols and the crosslinking triols can provide an effective reaction media for preparing a viscoelastomeric thermoset polymer 110 uniquely possessing the viscoelastic, adhesiveness, cohesiveness, releasability, cleansability, and antimicrobial features for the inventive flexible medical item container 100 of the present disclosure. It has also been discovered herein that the resulting polymer 110 further possesses a resistance to melting when subjected to heat.

In general, the straight chain polyol component of the viscoelastomeric thermoset polymer 110 can provide straight chain infrastructure formation and sufficient crosslinkage disruption to permit for a highly effective intermolecular plasticizer attraction and alignment, thus providing for an unusually high and effective loading of the viscoelastic, adhesive, cohesive and antipathogenic contributing plasticizer co-factors. In some preferred embodiments, the straight chain polyol can be provided by a polyether diol having a molecular weight suitably ranging from about 1,000 to about 10,000, such as about 1,000 to about 8,000, or about 2,000 to about 6,000 for improved benefits, and preferably having two (2) terminal reactive groups (e.g., hydroxyl groups). Such polyether diol can be suitably present in an amount ranging from about 1 wt % to about 65 wt % of the total reaction media weight, such as about 5 wt % to about 55 wt %, or about 10 wt % to about 45 wt % of the total reaction media weight, to provide improved benefits. In one example, a 2-functional polyether diol, designated as ELASTOCAST C-4057, available from BASF Corporation, can provide a suitable straight chain polyol component to form the viscoelastomeric thermoset polymer 110 component of the inventive flexible medical item container 100.

In general, the crosslinking polyol component of the viscoelastomeric thermoset polymer 110 can provide sufficient crosslinkage infrastructure to the polymer 110, and can contribute to the unexpected cohesiveness, releasability and stability (i.e., inhibiting plasticizer bleeding) attributes thereof. In some preferred embodiments, the crosslinking polyol can be provided by a polyether triol having a molecular weight suitably ranging from about 1,000 to about 10,000, such as about 2,000 to about 8,000, or about 3,000 to about 7,000 for improved benefits, and preferably having three (3) reactive groups (e.g., hydroxyl groups, wherein two (2) of the reactive groups are terminal reactive groups). Such polyether triol can be suitably present in an amount ranging from about 3 wt % to about 50 wt % of the total reaction media weight, such as about 10 wt % to about 45 wt %, or about 20 wt % to about 40 wt % of the total reaction media weight, to provide improved benefits. In one example, a 3-functional polyether triol, designated as ELASTOCAST C-4018, available from BASF Corporation, can provide a suitable triol component to form the viscoelastomeric thermoset polymer 110 of the present disclosure.

The adhesiveness properties of the polymer 110 can be tailored to fit the need for any given medical items 150 to be attached to the flexible medical item container 100. Accordingly, the thermosetting reaction media may be properly formulated so as to impart a desired degree of adhesiveness for the adherence and stabilization of any given medical item 150 adhered to the container 100 while still retaining the desired cohesiveness of the polymer 110. For example, in general, increasing the straight chain polyol to crosslinking polyol weight ratio (e.g., increasing the diol content relative to the triol content) will result in an increased adhesiveness of the polymer 110. Conversely, decreasing the straight chain polyol to crosslinking polyol weight ratio (e.g., increasing the triol content relative to the diol content) will generally result in an increased cohesiveness of the polymer 110. Thus, controlling the straight chain polyol to crosslinking polyol weight ratio within the range of about 3:1 to about 1:3 for example can result in a polymer 110 having a desired adhesiveness and cohesiveness for the adhesion and subsequent release of any particular medical item 150.

The adhesive and cohesive viscoelastomeric thermoset polymer 110 also comprises a quantity of plasticizer typically ranging from about 10 wt % to about 60 wt % of the total reaction media weight, such as about 15 wt % to about 55 wt %, or about 20 wt % to about 50 wt % of the total reaction media weight, to provide improved benefits. More particularly, the plasticizer component includes a triglyceride plasticizer, and can optionally further include a process aid (i.e., reaction media viscosity reducing) plasticizer. In preferred embodiments, the triglyceride plasticizer is an epoxidized triglyceride plasticizer, and the optional viscosity reducing plasticizer is an ester plasticizer. The plasticizer components of the thermoset reaction media are typically liquid at room temperature (i.e., about 21° C.). It has been discovered herein that the weight ratio of triglyceride plasticizer to viscosity reducing plasticizer can suitably fall within a prescribed weight ratio range of about 1:0 to about 1:1, such as about 6:1 to about 1:3, or about 3:1 to about 1:2, to provide a workable reaction media viscosity for a particular application, and to help provide the desired viscoelastic, adhesiveness, cohesiveness, releasability, cleansability, and/or antipathogenic attributes of the resulting polymer 110. The content and type of plasticizers can have a pronounced effect upon imparting the desired polymer 110 attributes herein. Thus, a controlled amount of triglyceride plasticizer (e.g., epoxidized triglyceride plasticizer) and optional viscosity reducing plasticizer (e.g., ester plasticizer) within the prescribed range can provide an effective reaction media for preparing a polymer 110 uniquely possessing the desired compositional attributes for use herein. Desirably, the plasticizer component is uniformly dispersed and cohesively bound throughout the thermosetting reaction media (along with the other polymerizable thermosetting components) and will tenaciously remain uniformly dispersed within the resultant viscoelastomeric thermoset polymer 110 in a highly cohesive and stabilized (i.e., resistance to plasticizer leakage) form.

Suitable triglyceride plasticizers for preparing the viscoelastomeric thermoset polymer 110 desirably include epoxidized triglyceride plasticizers. Epoxidized triglyceride plasticizers, such as epoxidized animal oils and epoxidized vegetable oils, are particularly effective as a plasticizer component in the thermosetting viscoelastomeric reaction media herein. Amongst the suitable epoxidized triglyceride plasticizers, epoxidized vegetable oils (e.g., soybean, corn, cottonseed, *perilla*, safflower, linseed, tall, etc.) have been found to be particularly effective triglyceride plasticizers herein. Other suitable triglyceride plasticizers have been more extensively described in the aforementioned cross-referenced related applications. Such triglyceride plasticizers can be suitably present in an amount that is less than about 50 wt % of the total reaction media weight, such as less than about 45 wt %, or about 10 wt % to less than 50 wt %, or about 10 wt % to less than about 45 wt % of the total reaction media weight, to provide improved benefits. In one desirable example, epoxidized soybean oil can provide a highly suitable triglyceride plasticizer to form the viscoelastomeric thermoset polymer 110 of the present disclosure.

The adhesive and cohesive viscoelastomeric thermoset polymer 110 can also optionally comprise a suitable reaction media viscosity reducing plasticizer. In general, those plasticizers which are suitable as plasticizing agents for the plasticization of polyvinyl chlorides can be utilized as viscosity reducing plasticizers for the reaction media herein. Exemplary viscosity reducing plasticizers for preparing the polymer 110 can include, but are not limited to, ester plasticizers. Such ester plasticizers are especially effective as an optional additional plasticizer component in the thermosetting reaction media. Suitable ester plasticizers typically have a relatively low molecular weight, typically less than about 750, or less than about 500, and can include, but are not limited to, the condensation products of alcohols (e.g., $C_1$-$C_{10}$ alcohols, such as $C_2$-$C_6$ alcohols) and dicarboxylic acids (e.g., $C_2$-$C_{12}$ dicarboxylic acids, such as $C_4$-$C_8$ dicarboxylic acids). In addition, amongst the more fluid ester plasticizers, such as diester plasticizers for example, are the lower dialkyl esters of dicarboxylic acids, such as dialkyl esters having alkyl groupings of less than 12 carbon atoms, such as $C_1$-$C_8$ dialkyl ester groupings of sebacates, adipates, phthalates, isophthalates, maleates, azelates, glutarates, etc., which have been found to be particularly effective ester plasticizers herein.

In some aspects, the polar strength (often referred to as "dipole moment") of such ester plasticizers depends, to a certain degree, upon the alcohol condensation reactant chain length, which can also have an effect upon the adhesiveness characteristics of the thermoset viscoelastomeric reaction product (i.e., the polymer 110). For example, non-epoxidized plasticizers having a relatively high dipole moment (e.g., dibutyl sebacate, having a dipole moment of 2.48 debyes (D), as compared to epoxidized plasticizers having a dipole moment near 0 D) can be effective in retaining the desired properties of the polymerizate while also providing a thermosetting reaction media exhibiting a reduced working viscosity, which is particularly effective for use in permeating porous interstices or fabric structures of an object 170 (such as a surgical drape, for example). Suitable ester plasticizers can have a dipole moment of greater than about 1.5 D, such as greater than about 2.0 D, to provide improved benefits. The ester plasticizers can be suitably present in an amount ranging from about 0 wt % to about 40 wt % of the total reaction media weight, such as about 1 wt % to about 30 wt %, or about 2 wt % to about 20 wt % of the total reaction media weight for improved benefits. In one non-limiting example, dibutyl sebacate can provide a highly suitable ester plasticizer to form the reaction media of the present disclosure.

In some aspects, the incorporation (within the ranges prescribed herein) of the relatively low molecular weight ester plasticizer in combination with the triglyceride plasticizer (e.g., epoxidized triglyceride plasticizer) can be utilized herein to provide an easier fabricating form (e.g., for casting, molding, injecting, pouring, spraying, printing, etc.) of the uncured polymer mix (i.e., reaction media) by lowering the viscosity of the reaction media without adversely affecting the desirable features of the adhesive and cohesive viscoelastomeric thermoset polymer 110. For example, the addition of polar ester plasticizers, or substitution of the triglyceride plasticizers with polar ester plasticizers, has been found to effectively reduce the viscosity of the reaction media while still maintaining a desired level of adhesiveness and cohesiveness of the resulting polymer 110, as well as maintaining excellent releasability and stability properties. It has been discovered herein that including an ester plasticizer having a fluidic consistency at room temperature (i.e., about 21° C.) and having a relatively low molecular weight (e.g., less than about 750) in the reaction media can contribute to ideal working viscosities during the initial curing stages, rendering the reaction media to be more effective (e.g., from a viscosity standpoint) for forming the inventive flexible medical item container 100 of the present disclosure, particularly when in a prefabricated form.

As referenced above, the plasticizer component is desirably uniformly incorporated into the thermosetting reaction media (along with the other polymerizable thermosetting reactants) and will tenaciously remain uniformly dispersed within the resultant viscoelastomeric thermoset polymer 110 herein in a highly cohesive and stabilized form. The straight chain polyols and crosslinking polyols, in cooperative combination with the plasticizer, create a viscoelastic thermoset polymeric structure possessing a suitable degree of compositional releasable adhesiveness and cohesiveness which is desirable to adhesively secure and retain medical items 150, while also allowing for a clean cohesive separation of the medical items 150 from the polymer 110 (upon application of a sufficient counteracting force to the medical items 150 which overcomes the adhesive force of the polymer 110), desirably leaving no visually detectable polymeric residue on the medical items 150, and more preferably leaving no polymeric reside on the medical items 150 whatsoever. Controlling the reaction media weight ratio of triglyceride plasticizer and optional ester plasticizer (along with the straight chain polyol to crosslinking polyol weight ratios) accordingly constitutes an important consideration in preparing the reaction media for the adhesive and cohesive viscoelastomeric thermoset polymer 110 component of the inventive container 100. For example, if the amount of plasticizer is excessively high (i.e., outside the range prescribed herein), the resultant polymer 110 will tend to lose its desired cohesiveness and will then tend to permanently distort (i.e., may not return to its original innate form as when initially formed), and/or will tend to bleed plasticizer. However, it has been discovered herein that in certain instances, increasing the crosslinking polyol content can partially arrest such plasticizer bleeding, but such crosslinking polyol increase will then tend to decrease the adhesiveness of the polymer 110.

The unique bridged crosslinked polymeric structure (e.g., crosslinking triols separated by straight chain diols) of the thermoset polymerizate 110 obtained from an appropriate thermoset reaction media provides an ideal infrastructure for effectively harboring the plasticizer in an unexpectedly superior cohesive and adhesive form. Indeed, it appears that the crosslinked infrastructure and the polarity provided by the polymerized straight chain polyols and crosslinking polyols orients the polarized plasticizer within the resulting polymer 110 so as to impart, *inter alia*, the unexpected viscoelasticity, adhesiveness, cohesiveness, stability, cleansability and antimicrobial properties to the polymer 110 herein.

The adhesive and cohesive viscoelastomeric thermoset polymer 110 can also optionally comprise additional constituents including, but not limited to, catalysts, initiators, other additional plasticizers, colorants, UV inhibitors, antioxidants, and the like, as would be known to persons having ordinary skill in the art, without departing from the scope of the invention. For example, the polymerization of the thermosetting reaction media can be carried out in the presence of a catalyzing amount (defined above) of a catalyst (e.g., a slow-acting catalyst or a heat-activated catalyst) to control the curing rate of the reaction media. Suitable catalysts can include tertiary amines, tertiary phosphines, strong bases (e.g., alkali, alkaline earth metal hydroxides, alkoxides, phenoxides, etc.), acidic metal salts of strong acids, metal chelates, metal alcoholates, metal phenolates, organic acid salts, organo metallic derivatives, etc. In one non-limiting example, COSCAT 83 (available from Vertellus Holdings LLC, having a place of business located in Zeeland, Michigan, USA), which is a slow-acting organobismuth catalyst, can provide a suitable catalyst for controlling the curing rate of the thermosetting reaction media to form the adhesive and cohesive viscoelastomeric thermoset polymer 110. In another non-limiting example, FOMREZ CATALYST UL-29 (available from Momentive Performance Materials Inc., having a place of business located in Wilton, Connecticut, USA), which is a heat-activated tin thioglycolate catalyst, can provide a suitable catalyst for controlling the curing rate of the thermosetting reaction media to form the viscoelastomeric thermoset polymer 110.

Procedurally, the reaction product which forms the adhesive and cohesive viscoelastomeric thermoset polymer 110 can be prepared from a thermosetting reaction media homogeneously loaded with plasticizer(s) which includes a triglyceride plasticizer (preferably an epoxidized triglyceride plasticizer, such as epoxidized vegetable oil) as well as optionally any other effective polar plasticizer, coupled with a carefully measured amount of straight chain polyols (e.g., diols) and crosslinking polyols (e.g., triols) to create the necessary bridging between the crosslinks, and an isocyanate prepolymer hardener (e.g., diisocyanate, such as aliphatic, aromatic, heterocyclic, etc., polyisocyanates, cycloaliphatic isocyanates and arylaliphatic isocyanates), and typically in the presence of an appropriate catalyst (e.g., preferably a relatively slow acting catalyst). The reaction media desirably contains the necessary plasticizer loading specifically adapted to provide a curable reaction media, which upon curing, produces a viscoelastomeric reaction product (i.e., polymer 110) having a unique polymerizate structure effectively loaded with polar oriented plasticizers uniformly and homogeneously distributed throughout the polymer's entire thermoset mass, intertwined therewithin, and supported by the flexible plasticizer-entrapping thermoset polymerizate structure. Under the most effective thermosetting and fabricating conditions, the thermosetting polymerizate reactants and the plasticizers are collectively provided in the reaction media as liquids at room temperature (i.e., about 21° C.) without necessitating the use of any solvents, other chemical dispersion aids or elevated temperatures, in order to homogeneously disperse the reaction media components. Accordingly, this allows the thermosetting reaction to be effectively conducted at room temperature.

The crosslinked polymeric structure of the adhesive and cohesive viscoelastomeric thermoset polymer 110 obtained from an appropriate thermosetting reaction media provides an ideal infrastructure for effectively harboring plasticizer components in an unexpectedly desirable viscoelastic, adhesive, cohesive and stabilized polymeric form, while also providing unexpected antimicrobial properties and cleansability/reusability properties, as well as a resistance to melting when subjected to heat. Desirably, the plasticizer is uniformly incorporated throughout the reaction media containing the polymerizable components, and remains uniformly dispersed within the resultant polymer 110 in a highly cohesive form, thus preventing leakage of the plasticizers therefrom. It appears that the crosslinked infrastructure and the polarity provided by the polymerized straight chain polyols (e.g., polyether diols) and crosslinking polyols (e.g., polyether triols) orients the polarized plasticizer components (e.g., epoxidized triglyceride plasticizer and optional ester plasticizer) within the resulting polymer 110 to impart the unexpected viscoelastic, adhesiveness, cohesiveness, releasability, stability, cleansability, reusability and antimicrobial properties to the polymer 110 herein. Thus, the thermosetting straight chain polyols and crosslinking polyols in cooperative combination with the plasticizer create a thermoset polymeric structure possessing a high degree of compositional adhesiveness and cohesiveness for effective usage with the inventive flexible medical item containers 100 of the present disclosure, while also allowing for a clean cohesive separation of medical items 150 therefrom (i.e., leaving essentially no polymeric residue on the medical items 150).

From a molecular infrastructure standpoint, the unique combination of straight chain and crosslinking reactants and plasticizer types in the amounts prescribed herein creates a uniquely different and unique polymer 110. The appropriate control of straight chain polyol and crosslinking polyol reactants appears to create long chain polarized sites ideal for powerful cohesive polar entrapment of the plasticizer while also aligning the polarized plasticizer components in a powerful adhesive and cohesive positioning within the polymer 110. The polarized molecular alignment of the plasticizer cofactor within the polymeric infrastructure contributes to a highly cohesive structure which maintains its molecular integrity when subjected to forces which effect separation of the polymer 110 from a contacting surface of a medical item 150. The plasticizer appears to also be a major contributing factor in the polymer's unique viscoelastomeric properties. As a result, the viscoelastomeric thermoset polymer 110 possesses a host of unexpectedly unique and superior properties (e.g., adhesiveness, cohesiveness, releasability, stability, cleansability, reusability, antimicrobial, etc.) over conventional adhesive polymers currently available.

As referenced above, the thermoset prepolymer (e.g., isocyanate prepolymer), the straight chain linking polyols (e.g., diols) and the crosslinking polyols (e.g., triols), in cooperative combination with the plasticizer, create a polymer 110 having antimicrobial properties, as well as a thermoset viscoelastic polymeric structure possessing a high degree of compositional adhesiveness and cohesiveness necessary to adhesively secure and retain medical items 150, in addition to a clean cohesive separation from the medical items' 150 surfaces. The type of plasticizers and reactants in controlled amounts (i.e., within the quantity ranges prescribed herein) can also be effectively utilized to provide desirable thermosetting fabrication conditions for preparing the polymer 110, and thereby providing inventive flexible medical item containers 100 possessing the unique attributes herein.

As a result of its unique chemical composition and processing conditions, the viscoelastic thermoset polymer 110 component of the inventive flexible medical item container 100 herein possesses a host of unique and unexpected properties. For example, the polymer 110 exhibits advantageously unique viscoelastic properties. Due to its fluidic properties (as opposed to compression properties, such as found in foam or rubber compositions), such viscoelastic properties allow the polymer 110 to at least partially surround and conform to the configuration of a medical item 150 due to the weight of such item 150 and/or force exerted when a user places the item 150 upon the polymer 110 component of the containers 100 herein. The result is an increased contacting surface area of the medical items 150 for better adhesion and adhesive performance. This provides a significant advantage over conventional adhesive products (which typically exhibit compression properties as opposed to viscoelastic properties).

In addition, the polymer 110 component of the inventive flexible medical item container 100 herein also exhibits advantageously unique releasable adhesiveness properties. The overall tackiness or adhesiveness of the polymer 110 and its concomitant releasability characteristics can be effectively altered so as to match the needs of a particular medical item 150 by changing the compositional makeup of the thermosetting reaction media, particularly the straight chain polyol to crosslinking polyol reaction media weight ratio, as well as the reaction media plasticizer content and the types of plasticizers. For example, an increase in the amount of straight chain polyol (with respect to the amount of crosslinking polyol) will tend to increase the adhesiveness of the polymer 110, and thus also increase the amount of force required to release a medical item 150 from the polymer 110. Conversely, an increase in the amount of crosslinking polyol (with respect to the amount of straight chain polyol) will tend to decrease the adhesiveness of the polymer 110, and thus also decrease the amount of force required to release a medical item 150 from the polymer 110. In the case where the amount of straight chain polyol (with respect to the amount of crosslinking polyol) is increased, it has been found herein that a slight increase in the amount of prepolymer will generally serve to balance the reaction media reactants. In general, inventive flexible medical item containers 100 comprising the polymer 110 having a relatively high degree of adhesiveness will tend to be less effective for releasing relatively small, light and/or fragile medical items 150, but will tend to be more effective for adhering and stabilizing relatively larger, heavier and/or odd-shaped medical items 150. Typically, the adhesiveness of the polymer 110 component of this disclosure (and thus of the inventive flexible medical item container 100 herein) will desirably range from about 25 gf/cm 2 to about 150 gf/cm 2 as measured by the Adhesiveness & Cohesiveness Test, such as about 40 gf/cm 2 to about 100 gf/cm 2 to provide improved benefits.

Another unique advantage of the inventive flexible medical item container 100 herein resides in the manner in which the viscoelastomeric thermoset polymer 110 component will adhesively interact with medical items 150 which are adhesively attached thereto. The polymer 110 component's adhesive interaction with medical items 150, when such items 150 are placed thereupon, typically exhibits a slight initial increase in adhesiveness within about 5 to about 10 seconds after the initial adhesive attachment of a medical item 150 to the polymer 110 component, which is then followed by a stabilization to about 90% of its maximum or ultimate adhesive attraction within about 60 seconds after the initial adhesive attachment of the item 150 to the polymer 110 component. This slight change in adhesiveness may be indicative of an intermolecular realignment, coordinate covalent bonding, polarization of the plasticizing components, or some other molecular interaction therein. This subsequent adhesive increase may also be due to the viscoelastomeric properties of the polymer 110 component, which due to adhesive cradling of an adhered medical item 150, will provide added interfacing surface contacting area with the adhered item 150, resulting in an increase and subsequent stabilization of the adhesive attraction therebetween.

Another unique advantage of the inventive flexible medical item container 100 herein resides in the retention of at least its adhesiveness and cohesiveness properties. Surprisingly, the adhesive and cohesive viscoelastomeric thermoset polymer 110 component of the container 100 as provided by this invention retains a substantially unchanged degree of adhesiveness and cohesiveness with respect to adhered medical items 150 over prolonged periods of time (e.g., at least six (6) weeks or more), such as measured by the Adhesiveness & Cohesiveness Test. This provides another significant advantage over conventional adhesive products (wherein the adhesiveness and/or cohesiveness tends to degrade over time).

In addition, the polymer 110 component of the inventive flexible medical item container 100 herein also exhibits advantageously unique cohesiveness properties. For example, upon exposure to a counteracting force sufficient to overcome the adhesive attraction between a medical item 150 and the inventive flexible medical item container 100 herein (e.g., pulling an adhesively engaged item 150 away from the polymer 110 component to disengage the item 150), the compositional cohesiveness of the polymer 110 component will tenaciously retain its viscoelastomeric structural integrity by cohesively releasing substantially cleanly (i.e., without leaving substantially any polymeric residue) from the item 150 and then returning to its original innate form as prior to engagement of the item 150. This provides a significant advantage with respect to reusability and effectiveness of the adhesive container 100, as compared to conventional adhesive products (which typically do not return to their same innate form and/or leave visible residue upon a detached item and/or are not reusable (i.e., without experiencing a reduction in effectiveness)).

In addition, the polymer 110 component of the inventive flexible medical item container 100 herein also exhibits advantageously unique releasability properties. More particularly, the polymer 110 component possesses a tenacious internal compositional cohesiveness which provides an ability to release substantially cleanly away from a medical item 150 upon which it comes into contact, substantially without leaving any residue of the polymer 110 remaining on the surface of the item 150. (As used herein, the term "substantially" means that on a microscopic level, a nominal amount of polymeric residue may potentially be detectable.) Indeed, upon exposure to a suitable adhesive separating release force (e.g., pulling an adhesively engaged medical item 150 away from the polymer 110), the compositional cohesiveness of the polymer 110 component will tenaciously retain its viscoelastic structural integrity by separating substantially cleanly from the surface of a medical item 150 upon which it has come into contact (i.e., without leaving more than a trace of polymeric residue upon the surface). Accordingly, upon adhesive separation from such surface of a medical item 150, the polymer 110 component will return to its substantially intact and innate form as prior to adherence of the item 150, while leaving no more than a minuscule amount of polymeric residue adhering upon the item 150. More typically, upon separation from the surface of a medical item 150, there will exist no polymeric residue remaining upon the item 150 whatsoever. This provides yet another significant advantage over conventional adhesive products (which typically leave a visually detectable amount of residue upon the surface of an item upon which it comes into contact).

During the removal of a medical item 150 from the polymer 110 component of the inventive flexible medical item container 100 of the present disclosure, it has been observed herein that the polymer 110 tends to pull away from the surface of the item 150 until the polymer 110 completely separates (i.e., substantially breaks cleanly away) from the surface, and then the polymer 110 component forthrightly cohesively returns to its original or innate form as prior to the item's 150 adherence thereto. The extent of temporary distortion exhibited by the polymer 110 component upon exposure to separation forces from the surface of a medical item 150 will depend largely upon the adhesiveness, cohesiveness and viscoelastic properties of the polymer 110. It has been further observed herein that, upon coming into contact with a surface of a medical item 150, a polymer 110 herein having relatively higher adhesiveness values will physically tend to tenaciously string-out (similar to the pulling of heated candy taffy) until a clean adhesive, but cohesive, separation ultimately occurs from the surface of the item 150, whereupon the polymer 110 component then returns to its original innate form, leaving essentially no polymeric residue upon the item 150.

In addition, the polymer 110 component of the inventive flexible medical item container 100 herein also exhibits antimicrobial properties. For example, the polymer 110 can neutralize microbial pathogens (e.g., viruses, bacteria, germs, etc.) which may be present upon the engaged surfaces of a medical item 150. This provides still another significant advantage over conventional adhesive products (which typically do not exhibit such antimicrobial properties).

In addition, with reference to FIGS. 4A-4C, the polymer 110 component of the inventive flexible medical item container 100 herein also exhibits unique cleansability properties. For example, due to its adhesive nature, the polymer 110 component has a tendency to adhesively attract contaminants 190, such as airborne contaminants (e.g., dust, lint, debris, etc.) and/or patient derived contaminants (e.g., blood, saliva, hair, keratinocytes, etc.), which can potentially diminish adhesiveness (and potentially antimicrobial effectiveness) over time. However, the original adhesiveness and antimicrobial properties of the polymer 110 component can be easily restored via conventional washing and/or other suitable contaminant removal techniques. For example, unlike conventional adhesive products which must be discarded upon contamination (often after merely a single use), the polymer 110 component of the present invention can be cleansed from contaminants and restored to its substantially original adhesive, cohesive and antimicrobial efficacy. Surprisingly, conventional washing with water 195 or with a solution of water and common soap (e.g., rinsing, handwashing, scrubbing, washing machines, dishwashers, etc.), as well as autoclaving (i.e., applying high pressure steam), may be effectively utilized to eradicate and remove contaminants 190 therefrom and thereby permit fully functional continued use or re-use of the cleansed polymer 110 component. Accordingly, the inventive flexible medical item containers 100 and the polymer 110 component thereof are environmentally friendly, and may be considered as "green" technology as well. This provides yet another significant advantage over conventional adhesive products (which typically do not exhibit such cleansability and reusability capabilities).

In some embodiments, the viscoelastomeric thermoset polymer 110 can be prefabricated into a desired form (e.g., desired shape profile, dimensions, etc.) using various techniques as known to persons having ordinary skill in the art. Such prefabrication techniques can include, but are not limited to, casting, molding, pouring, injecting, film forming, brushing, spraying, and the like. Prefabrication of the polymer 110 typically comprises first preparing the thermosetting reaction media, then utilizing a desirable prefabrication process while the reaction media is in a liquid or semi-liquid (i.e., partially cured) form, and subsequently allowing the reaction media to fully cure to form the polymer 110. This can be accomplished, *inter alia*, by disposing liquid reaction media (i.e., uncured or partially cured) into a suitable mold and then curing the reaction media to form the polymer 110 component, or by pouring the reaction media onto a suitable surface (e.g., a flat surface) as a layer of the reaction media, allowing it to fully cure, and then cutting the polymer 110 into components therefrom. Other methods for forming the polymer 110 component which will be apparent to persons having ordinary skill in the art are also suitable, without departing from the scope of the invention. Such prefabricated form of the polymer 110 can have any shape profile and dimensions as may be desired without departing from the scope of the invention, including those known to persons having ordinary skill in the art, such as a pad, a substrate, a strip, a sheet, a film, an overlay, a mat, a random shape, and the like.

It has been discovered herein that certain materials, such as silicone-coated materials or halogenated polymers (e.g., polyvinylchloride (PVC)) (except for special formulations) are generally less adhesively compatible (as compared to most other materials) with the adhesiveness properties of the adhesive and cohesive viscoelastomeric thermoset polymer 110 herein (i.e., the polymer 110 does not adhere well to such materials). As a result, such less adhesively compatible materials can provide excellent release properties from the polymer 110, which renders such materials particularly effective for use as a mold material which can be utilized to cure the reaction media and thus prefabricate the polymer 110 component (as well as for removable protective covering members 130,140). However, it should be understood that if such less adhesively compatible materials have a porous, fabric or patterned structure, such structures can provide anchoring or penetration sites for the polymer 110 component (e.g., due to the polymer's 110 viscoelastic nature), thus increasing the adhesion between the polymer 110 and such materials, rendering such materials to be unsuitable for use as a mold material (or removable protective covering members 130,140).

Referring now to FIGS. 6A-7B, in another preferred embodiment of the inventive flexible medical item container 100, the invention can be in the form of an integrated flexible medical item container 100, which can be integrated with an object 170, such as those objects described above. In comparison to the embodiment described above, the inventive flexible medical item container 100 of this embodiment can be provided to a user as a container/object combination, wherein the container 100 has already been disposed upon the object 170 at a predetermined location (preferably proximate or adjacent to the intended location of a medical, dental or hygienic procedure) when received by the user.

In preferred aspects of this embodiment, the adhesive and cohesive viscoelastomeric thermoset polymer 110 of the inventive flexible medical item container 100 is essentially equivalent to the polymer 110 as described above for the prefabricated embodiment. However, rather than prefabricating the viscoelastomeric thermoset polymer 110 component, the polymer 110 can be formed in combination with a particular object 170, (e.g., a surgical drape). This can be accomplished by first disposing a quantity of uncured or partially cured reaction media (i.e., while the reaction media is still in liquid form) directly onto a surface of an object 170, optionally allowing the reaction media to soak at least partially into the object 170 (such as where the object 170 has a porous structure) (see e.g., FIGS. 6B-6C), and then allowing the reaction media to fully cure in-situ to form the adhesive and cohesive viscoelastomeric thermoset polymer 110, and thus the inventive flexible medical item container 100. It has been discovered herein that in such "in situ" embodiments, the polymer 110 tends to form a stronger bond with the object 170 upon which it is applied (regardless of whether or not the object 170 is porous or comprises anchoring sites), as compared the merely adhesive bonding of the prefabricated form. It is believed that in such in situ embodiments, attachment of the polymer 110 to the object 170 includes additional bonding (e.g., chemical bonding) to the object 170, in addition to the adhesive bonding common to both the in situ embodiments and the prefabricated embodiments. The reaction media of this embodiment can be applied to an object 170 using techniques as would be known to persons having ordinary skill in the art, including pouring, printing, calendaring, casting, brushing, spraying, dipping, and the like. The polymer 110 component, and thus the inventive flexible medical item container 100, of this embodiment can comprise any functional shape profile or form, such as a coating, a strip, a pattern, a random shape, an integrated film, and the like, without departing from the scope of the invention.

Figure 6C:
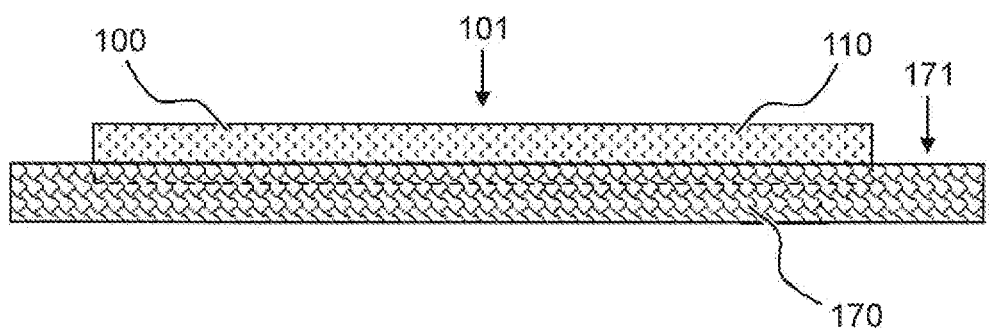
FIG. 6C is an alternative side view showing the flexible medical item container of FIG. 6A as taken along line D-D, wherein the polymer component is disposed partially into the object.

As referenced above, where the object 170 comprises a porous material, the polymer 110 component can optionally be disposed at least partially into the object 170 (see e.g., FIG. 6C). For example, uncured or partially-cured reaction media can be applied to a porous surface of an object 170 and allowed to at least partially soak into the interior structure of the object 170. The reaction media can then be allowed to fully cure in situ (relying on adhesive bonding, chemical bonding and interactions within the interior structure of the article 150 (e.g., friction, etc.)) for attachment of the inventive flexible medical item container 100 to the objects 170. In such aspects of this embodiment, the inventive container 100 typically cannot be removed from the object 170.

Substantially all of the properties and advantages of the prefabricated inventive flexible medical item container 100 described above apply equally to the integrated inventive flexible medical item container 100 of this embodiment, including the viscoelastic, adhesiveness, releasability, cohesiveness, stability, cleansability and antimicrobial properties. However, while reusability is an option for this embodiment, it is less likely to be utilized as compared to the prefabricated embodiment.

Although the embodiments shown in FIGS. 6A-6C are illustrated to have a generally rectangular shape profile, it should be understood that the inventive flexible medical item container 100 of this embodiment can have any functional shape profile known to persons having ordinary skill in the art (e.g., square, trapezoidal, triangular, circular, ovular, a strip, random, etc.) without departing from the scope of the invention. In addition, the flexible medical item container 100 of this embodiment can have any suitable dimensions as may be desired for a particular use. For example, in the case of the medical item container 100 having a generally rectangular profile, the medical item container 100 may comprise a length (as measured along the x-axis 1) of about 75 cm and a width (as measured along the y-axis 2) of about 40 cm, such as a length of about 50 cm and a width of about 30 cm, or a length of about 40 cm and a width of about 25 cm, or other desired dimensions for a particular use. The integrated flexible medical item container 100 of this embodiment can also comprise a height or thickness (as measured along the z-axis 3). There are no particular limits to the thickness, however the thickness of this embodiment may be less than the prefabricated embodiment described above. Accordingly, in the case of an integrated medical item container 100, the thickness will typically range from about 0.5 mm to about 8 mm as measured from the top side 171 surface of the object 170 to the top side 101 of the container 100, such as from about 0.75 mm to about 3 mm. It should be understood that the thickness can be less than 0.5 mm or greater than 8 mm for an integrated medical item container 100 without departing from the scope of the invention, but such extra thickness generally does not add any benefit to the invention. In addition, it should be understood that the thickness can be uniform or non-uniform without departing from the scope of the invention.

Similar to the prefabricated embodiment, the adhesiveness of the inventive flexible medical item container 100 of this embodiment can likewise be formulated to be about 25 gf/cm 2 to about 150 gf/cm 2, as measured by the Adhesiveness & Cohesiveness Test, such as about 40 gf/cm 2 to about 100 gf/cm 2 to provide improved benefits. However, since the container 100 of this embodiment has been integrated with an object 170, and thus comprises additional bonding thereto (i.e., at least adhesive bonding and chemical bonding), the potential need to further include an additional adhesive component 120 is greatly diminished or non-existent.

Figure 7A:
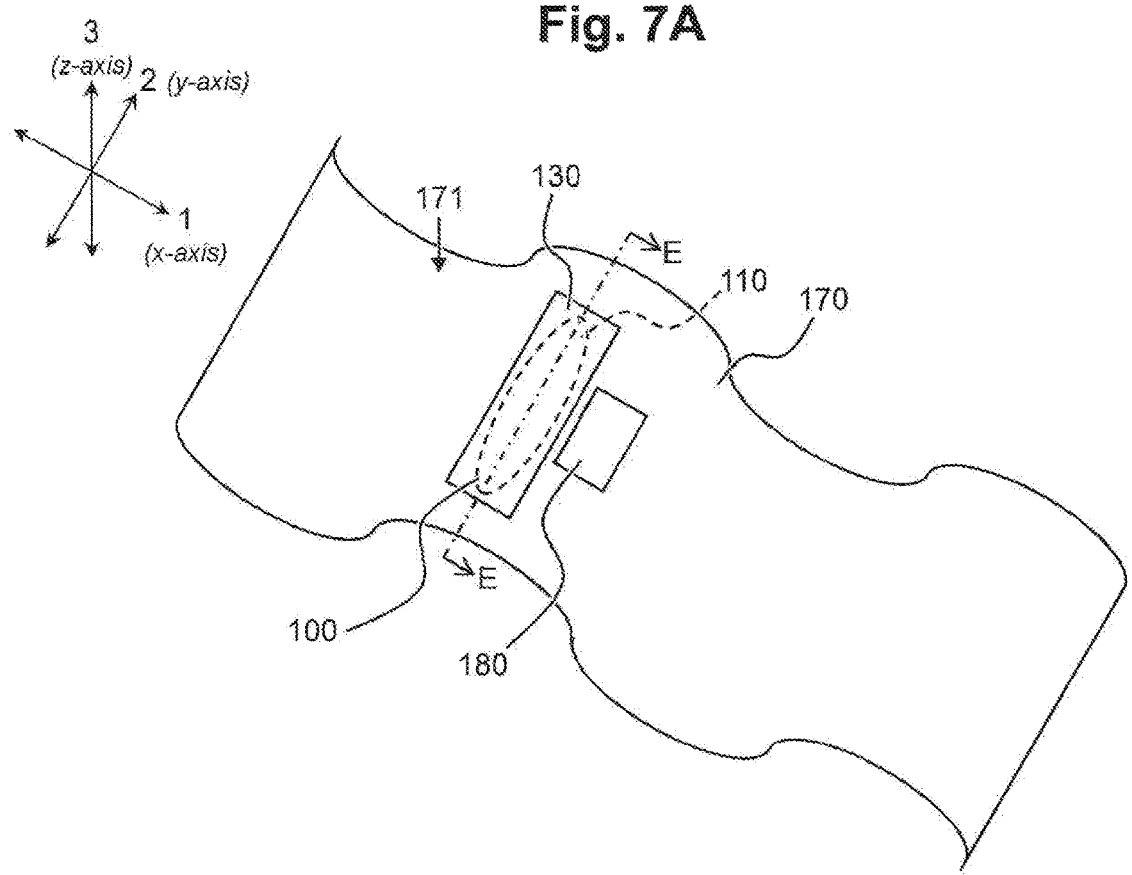
FIG. 7A is a perspective view showing a non-limiting exemplary embodiment of an inventive flexible medical item container comprising an optional top side removable protective covering member.
Figure 7B:
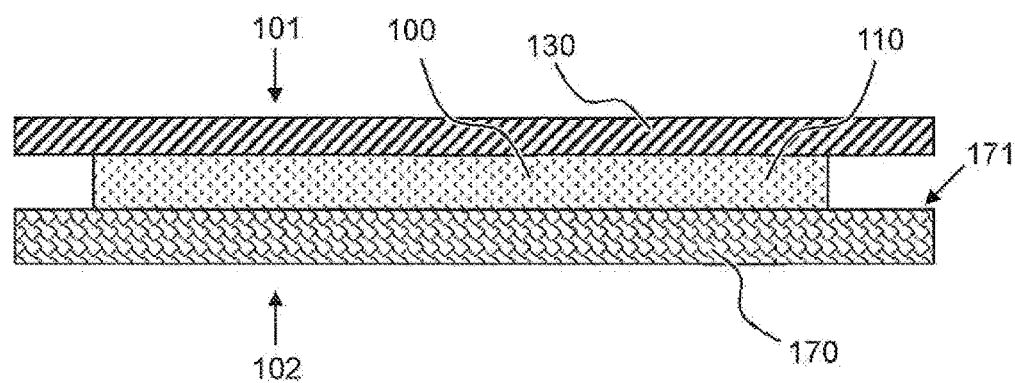
FIG. 7B is a side view showing the flexible medical item container of FIG. 7A as taken along line E-E.

Referring now to FIGS. 7A-7B, in some aspects, due to at least the inventive flexible medical item container's 100 inherently adhesive nature, as well as its intended use in hygienic or sterilized environment, it may be desirable to dispose an optional top side removable protective covering member 130 upon the top side 101 of the container 100. For example, such protective covering member 130 can allow for effective shipment of the container 100, ease of handling the container 100 (e.g., preventing the container 100 from adhering to a user's hands), and can prevent undesired contamination of the container 100 by contaminants 190 prior to its intended use. In some aspects, such protective covering member 130 can also be useful as packaging materials for the invention. Such protective covering member 130 can comprise any suitable material which can be completely (and preferably relatively easily) removed from the top side 101 of the container 100 without leaving any covering materials upon the container 100 during removal. For example, materials which have a relatively low or incompatible adhesive affinity to the medical item container 100 can be used with the invention to provide a suitable protective covering member 130 for the exposed top side 101 surface of the container 100. Examples of a suitable protective covering member 130 can include, but is not limited to, silicone-coated substrates, polyvinyl chloride (PVC) films, paraffin-coated substrates, TEFLON-coated substrates, and the like, which tend to be less adhesively compatible with the inventive container 100 than most other materials.

The invention also includes a first method for forming an inventive flexible medical item container 100. The method comprises:

A. providing a reaction media comprising about 2 wt % to about 10 wt % isocyanate prepolymer, about 35 wt % to about 75 wt % polyols comprising about 1 wt % to about 65 wt % straight chain polyols (based on the total reaction media weight) and about 3 wt % to about 50 wt % crosslinking polyols (based on the total reaction media weight), and about 10 wt % to about 60 wt % plasticizer comprising about 10 wt % to less than about 45 wt % epoxidized triglyceride plasticizer (based on the total reaction media weight) and about 0 wt % to about 40 wt % viscosity reducing plasticizer (based on the total reaction media weight);
B. providing a suitable mold (not shown);
C. disposing the reaction media into the mold while in liquid (i.e., an uncured or partially-cured) state;
D. allowing the reaction media to fully cure into an adhesive and cohesive viscoelastomeric thermoset polymer 110; and
E. removing the polymer 110 from the mold to provide a prefabricated inventive flexible medical item container 100 of the present disclosure.

In some aspects of this embodiment, the method can optionally include disposing a quantity of an addition adhesive component 120 onto the bottom side 102 of the container 100. In other aspects, the method further comprises disposing medical items 150 upon a top side 101 of the flexible medical item container 100. In yet other aspects, the isocyanate prepolymer comprises a diisocyanate, the straight chain polyols comprise polyether diol, the crosslinking polyols comprise polyether triol, the epoxidized triglyceride plasticizer comprises epoxidized soybean oil, and the viscosity reducing plasticizer comprises dibutyl sebacate.

The invention also includes a second method for forming an inventive flexible medical item container 100. The method comprises:

A. providing a reaction media comprising about 2 wt % to about 10 wt % isocyanate prepolymer, about 35 wt % to about 75 wt % polyols comprising about 1 wt % to about 65 wt % straight chain polyols (based on the total reaction media weight) and about 3 wt % to about 50 wt % crosslinking polyols (based on the total reaction media weight), and about 10 wt % to about 60 wt % plasticizer comprising about 10 wt % to less than about 45 wt % epoxidized triglyceride plasticizer (based on the total reaction media weight) and about 0 wt % to about 40 wt % viscosity reducing plasticizer (based on the total reaction media weight);
B. providing a suitable object 170;
C. disposing the reaction media upon the top side 171 of the object 170 while in an a liquid (i.e., uncured or partially-cured) state; and
D. allowing the reaction media to fully cure in-situ into an adhesive and cohesive viscoelastomeric thermoset polymer 110 to provide an integrated inventive flexible medical item container 100 of the present disclosure.

In some aspects of this embodiment, the method further comprises disposing medical items 150 upon a top side 101 of the flexible medical item container 100. In other aspects, the isocyanate prepolymer comprises a diisocyanate, the straight chain polyols comprise polyether diol, the crosslinking polyols comprise polyether triol, the epoxidized triglyceride plasticizer comprises epoxidized soybean oil, and the viscosity reducing plasticizer comprises dibutyl sebacate.

The present invention may be better understood with reference to the following examples.

EXAMPLES

Example 1

A thermosetting reaction media suitably formulated to form the adhesive and cohesive viscoelastomeric thermoset polymer 110 component of the inventive flexible medical item container 100 of the present disclosure was prepared by uniformly admixing together a two-part solution component mix (Part A Solution and Part B Solution) comprising:

| | Percent by Weight: |
|---|---|
| Part A Solution - Ingredients: | |
| Methylene diphenyl diisocyanate-based glycol prepolymer (ElastoCAST TQZP23 available from BASF Corporation) | 6.02 wt % |
| Epoxidized triglyceride plasticizer (epoxidized soybean oil) | 43.98 wt % |
| Part B Solution - Ingredients: | |
| Polyether diol (ElastoCAST C-4057 available from BASF Corporation) | 16.89 wt % |
| Polyether triol (ElastoCAST C-4018 available from BASF Corporation) | 33.02 wt % |
| Colorant blend (1 part STAN-TONE 42ET02 Blue (available from Avient Corporation, having a place of business located in Avon Lake, Ohio, USA) and 5 parts epoxidized soybean oil) | 0.04 wt % |
| Slow-acting Catalyst (COSCAT 83 available from Vertellus Holdings LLC) | 0.05 wt % |
| Total | 100% |

A generally rectangular PVC mold having rounded corners was provided (not shown). The mold had an interior length of about 41 cm, an interior width of about 25 cm and an interior height (i.e., depth) of about 1 cm.

The Part A ingredients were then mixed to form the Part A Solution. Separately, the Part B ingredients were mixed to form the Part B Solution. Equal parts (i.e., a 1:1 ratio) of the Part A Solution and the Part B Solution were then combined and blended through a static mixer using metering pumps to form a thermosetting reaction media. While still in liquid form, a quantity of the resulting reaction media of this Example 1 was disposed into the mold until the height (as measured from the interior bottom of the mold) reached about 2 mm. The reaction media was then allowed to fully cure to form an adhesive and cohesive viscoelastomeric thermoset polymer 110. Upon fully curing, the polymer 110 was removed from the mold, thus forming a prefabricated inventive flexible medical item container 100 of the present disclosure in the form of a pad or mat.

Accordingly, the flexible medical item container 100 had a length of about 41 cm, a width of about 25 cm and a substantially uniform thickness of about 2 mm. It was observed that the container 100 of this Example 1 was relatively very flexible, and that the exterior surfaces of the container 100 felt sticky. The container 100 was placed in a laid-flat configuration onto an object 170 in the form of a wooden board which had been angled at approximately 45-degrees from horizontal. Several medical items 150 in the form of a metallic forceps, a metallic tweezers and a plastic syringe holder were then placed on the top side 101 of the container 100. Each medical item 150 was then subsequently removed and reattached several times. It was observed that the medical items 150 each detached relatively easily when a sufficient counteracting force was applied, and that the container 100 did not detach from the wooden board object 170 while detaching each medical item 150. It was also observed that subsequent reattachments of the medical items 150 after repeated removals did not exhibited any noticeable diminishing adhesion force (i.e., adhesiveness) between the medical items 150 and the inventive flexible medical item container 100. Upon visual inspection of each medical item 150, it was further observed that no polymeric residue was visually detectable upon any of the items 150.

Lastly, the adhesiveness and cohesiveness of the inventive flexible medical item container 100 of this Example 1 was tested in accordance with the Adhesiveness & Cohesiveness Test set forth herein. The average adhesiveness was measured to be about 50 gf/cm 2. It was also noted that no visually observable polymeric residue remained upon the surface 345 of the cylinder 340 component of the testing apparatus 300 after each test iteration (see FIG. 8).

Example 2

An object 170 in the form of a sheet of flexible SMS nonwoven material (i.e., spunbond/meltblown/spunbond laminate) was provided. The material had a length of about 50 cm, a width of about 30 cm and a thickness of about 0.1 mm. It was visually observed that the material appeared to comprise a relatively minute checkered pattern. The object 170 was placed in a laid-flat configuration upon a lab table.

A thermosetting reaction media was then prepared in accordance with Example 1 above. While still in liquid form, a sufficient quantity of the reaction media was relatively linearly poured onto the top side 171 of the object 170 (i.e., the SMS material) and gently spread to form a generally rectangular shape having a length of about 41 cm, a width of about 25 cm and a fairly uniform average thickness of about 2 mm. The reaction media was then allowed to fully cure in-situ upon the object 170, thus forming an inventive flexible medical item container 100 of the present disclosure integrated with an object 170.

It was observed that the container 100 and object 170 combination was relatively very flexible. It was also observed that the top side 101 of the container 100 felt sticky, but that the bottom side of the combination did not feel sticky. Upon inspecting the bottom side of the combination (i.e., the bottom side of the object 170), it was observed that no reaction media appeared to have soaked through the SMS material.

It was further observed that the flexible medical item container 100 could not readily be separated from the object 170 of this Example 2. This is likely due to both adhesive bonding and chemical bonding of the polymer 110 component of the container 100 to the top side 171 of the SMS material object 170, as well as the presence of anchoring sites inherent upon the SMS material.

Several medical items 150 in the form of a metallic forceps, a metallic tweezers and a plastic syringe holder were then placed on the top side 101 of the container 100. Each medical item 150 was then subsequently removed and reattached several times. It was observed that the medical items 150 each detached relatively easily when a sufficient counteracting force was applied, and that the SMS material object 170 did not require being separately held down while the medical items 150 were being detached. It was also observed that subsequent reattachments of the medical items 150 after repeated removals did not exhibited any diminishing adhesion force (i.e., adhesiveness) of the medical items 150 to the inventive flexible medical item container 100. Upon visual inspection of each medical item 150, it was further observed that no polymeric residue was visually detectable upon any of the items 150.

Lastly, the adhesiveness and cohesiveness of the container 100 of this Example 2 was tested in accordance with the Adhesiveness & Cohesiveness Test set forth herein. For this test sample 330, the container 100 and object 170 combination was secured to the testing platform 360 using adhesive tape (see FIG. 8). The average adhesiveness of the integrated container 100 was measured to be about 50 gf/cm 2. It was also noted that no observable polymeric residue remained upon the surface 345 of the cylinder 340 component of the testing apparatus 300 during each test iteration.

It will be appreciated that details of the foregoing examples, given for purposes of illustration, are not to be construed as limiting the scope of the present invention. Although only a few exemplary embodiments of the present invention have been described in detail above, persons having ordinary skill in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of the present invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. A flexible medical item container for releasably adhering medical items thereto comprising an adhesive and cohesive viscoelastomeric thermoset polymer.

2. The flexible medical item container of claim 1, further comprising antimicrobial properties.

3. The flexible medical item container of claim 2, further comprising cleansability properties for removing contaminants adhered thereto.

4. The flexible medical item container of claim 3, wherein a cleansing of the flexible medical item container is capable of being conducted via washing with water, and wherein such cleansing fully restores adhesiveness and antimicrobial properties of the flexible medical item container.

5. The flexible medical item container of claim 1, wherein no visually detectable amount of polymeric residue will be present upon a medical item adhered to the flexible medical item container upon removal of the medical item from the flexible medical item container.

6. The flexible medical item container of claim 1, further comprising a top side removable protective covering member disposed upon a top side of the flexible medical item container.

7. The flexible medical item container of claim 1, wherein the flexible medical item container is in the form of a prefabricated flexible medical item container.

8. The flexible medical item container of claim 7, further comprising a top side, a bottom side, and a distal edge which forms a periphery about the flexible medical item container.

9. The flexible medical item container of claim 8, wherein the bottom side is capable of being disposed upon and adhesively adhered to an object via adhesive bonding.

10. The flexible medical item container of claim 8, further comprising an additional adhesive component disposed upon the bottom side of the flexible medical item container, wherein the additional adhesive component comprises a greater adhesiveness than the bottom side of the flexible medical item container.

11. The flexible medical item container of claim 10, wherein the additional adhesive component comprises a pressure sensitive adhesive.

12. The flexible medical item container of claim 8, further comprising a bottom side removable protective covering member disposed upon the bottom side of the flexible medical item container.

13. The flexible medical item container of claim 7, further comprising a thickness of about 1 mm to about 10 mm.

14. The flexible medical item container of claim 1 wherein the adhesive and cohesive viscoelastomeric thermoset polymer is formed from a thermosetting reaction media comprising:
   A. about 2 wt % to about 10 wt % isocyanate prepolymer;
   B. about 35 wt % to about 75 wt % polyols; and
   C. about 10 wt % to about 60 wt % plasticizer;
   wherein the polyols comprise about 1 wt % to about 65 wt % straight chain polyols based on the total reaction media weight and about 3 wt % to about 50 wt % crosslinking polyols based on the total reaction media weight; and
   wherein the plasticizer comprises about 10 wt % to less than about 45 wt % epoxidized triglyceride plasticizer based on the total reaction media weight and 0 wt % to about 40 wt % viscosity reducing plasticizer based on the total reaction media weight.

15. The flexible medical item container of claim 14, wherein the isocyanate prepolymer comprises diisocyanate.

16. The flexible medical item container of claim 14, wherein the adhesive and cohesive viscoelastomeric thermoset polymer further comprises a straight chain polyol to crosslinking polyol weight ratio of about 3:1 to about 1:3.

17. The flexible medical item container of claim 14, wherein the straight chain polyols comprise polyether diol and the crosslinking polyols comprise polyether triol.

18. The flexible medical item container of claim 14, wherein the epoxidized triglyceride plasticizer comprises epoxidized vegetable oil plasticizer.

19. The flexible medical item container of claim 14, wherein the viscosity reducing plasticizer comprises an ester plasticizer.

20. The flexible medical item container of claim 19, wherein the ester plasticizer has a molecular weight of less than about 750.

21. The flexible medical item container of claim 14, wherein the ester plasticizer has a dipole moment of greater than about 1.5 D.

22. The flexible medical item container of claim 14, further comprising an object, and wherein the flexible medical item container is in the form of an integrated flexible medical item container.

23. The flexible medical item container of claim 22, wherein the reaction media has been disposed upon a top side of the object while in liquid form, and then allowed to fully cure in-situ to form the adhesive and cohesive viscoelastomeric thermoset polymer.

24. The flexible medical item container of claim 23, wherein the flexible medical item container is adhesively adhered to the object via at least adhesive bonding and chemical bonding.

25. The flexible medical item container of claim 24, wherein the flexible medical item container comprises a thickness of about 0.5 mm to about 8 mm.

26. The flexible medical item container of claim 1, wherein the flexible medical item container comprises an adhesiveness of about 25 gf/cm 2 to about 150 gf/cm 2.

27. A method for forming a flexible medical item container for releasably adhering medical items thereto, comprising:
   A. providing a reaction media comprising about 2 wt % to about 10 wt % isocyanate prepolymer, about 35 wt % to about 75 wt % polyols comprising about 1 wt % to about 65 wt % straight chain polyols based on the total reaction media weight and about 3 wt % to about 50 wt % crosslinking polyols based on the total reaction media weight, and about 10 wt % to about 60 wt % plasticizer comprising about 10 wt % to less than about 45 wt % epoxidized triglyceride plasticizer based on the total reaction media weight and 0 wt % to about 40 wt % viscosity reducing plasticizer based on the total reaction media weight;
   B. providing a mold;
   C. disposing the reaction media into the mold while in a liquid state;
   D. allowing the reaction media to fully cure into an adhesive and cohesive viscoelastomeric thermoset polymer; and
   E. removing the polymer from the mold to provide the flexible medical item container.

28. The method of claim 27, further comprising disposing medical items upon a top side of the flexible medical item container.

29. The method of claim 27, further comprising disposing a bottom side of the flexible medical item container upon an object.

30. The method of claim 29, further comprising disposing an additional adhesive component upon the bottom side prior to disposing the flexible medical item container upon the object.

31. The method of claim 27, wherein the isocyanate prepolymer comprises a diisocyanate, wherein the straight chain polyols comprise polyether diol, wherein the crosslinking polyols comprise polyether triol, wherein the epoxidized triglyceride plasticizer comprises epoxidized soybean oil, and wherein the viscosity reducing plasticizer comprises dibutyl sebacate.

32. A method for forming a flexible medical item container for releasably adhering medical items thereto, comprising:
- A. providing a reaction media comprising about 2 wt % to about 10 wt % isocyanate prepolymer, about 35 wt % to about 75 wt % polyols comprising about 1 wt % to about 65 wt % straight chain polyols based on the total reaction media weight and about 3 wt % to about 50 wt % crosslinking polyols based on the total reaction media weight, and about 10 wt % to about 60 wt % plasticizer comprising about 10 wt % to less than about 45 wt % epoxidized triglyceride plasticizer based on the total reaction media weight and 0 wt % to about 40 wt % viscosity reducing plasticizer based on the total reaction media weight;
- B. providing an object;
- C. disposing the reaction media upon at least a portion of the object while the reaction media remains in a liquid state; and
- D. allowing the reaction media to fully cure in-situ into an adhesive and cohesive viscoelastomeric thermoset polymer to provide the flexible medical item container.

33. The method of claim 32, further comprising disposing medical items upon a top side of the flexible medical item container.

34. The method of claim 32, wherein the isocyanate prepolymer comprises a diisocyanate, wherein the straight chain polyols comprise polyether diol, wherein the crosslinking polyols comprise polyether triol, wherein the epoxidized triglyceride plasticizer comprises epoxidized soybean oil, and wherein the viscosity reducing plasticizer comprises dibutyl sebacate.

* * * * *